(12) United States Patent
Garry et al.

(10) Patent No.: US 7,381,705 B2
(45) Date of Patent: Jun. 3, 2008

(54) INHIBITORS OF HEPATITIS C VIRUS

(75) Inventors: Robert F. Garry, New Orleans, LA (US); Jane A. McKeating, Birmingham (GB)

(73) Assignees: The Administrators Of The Tulane Educational Fund, New Orleans, LA (US); The Rockfeller University, New York, NY (US)

( * ) Notice: Subject to any disclaimer, the term of this patent is extended or adjusted under 35 U.S.C. 154(b) by 0 days.

(21) Appl. No.: 11/235,672

(22) Filed: Sep. 26, 2005

(65) Prior Publication Data

US 2006/0069027 A1 Mar. 30, 2006

Related U.S. Application Data

(60) Provisional application No. 60/614,280, filed on Sep. 29, 2004.

(51) Int. Cl.
   *A61K 38/16* (2006.01)
   *C07K 14/00* (2006.01)
   *C07K 7/08* (2006.01)
   *C07K 1/00* (2006.01)
   *C07K 2/00* (2006.01)
   *A61K 38/00* (2006.01)
   *A61K 38/02* (2006.01)

(52) U.S. Cl. .............. 514/12; 514/2; 514/13; 530/300; 530/324; 530/325; 530/326; 530/333

(58) Field of Classification Search .......... None
See application file for complete search history.

(56) References Cited

U.S. PATENT DOCUMENTS

| | | | |
|---|---|---|---|
| 5,747,239 A | 5/1998 | Wang et al. | |
| 6,030,785 A * | 2/2000 | Katze et al. | 435/6 |
| 6,037,348 A | 3/2000 | Colacino et al. | |
| 6,048,720 A * | 4/2000 | Dalborg et al. | 435/219 |
| 6,127,116 A | 10/2000 | Rice et al. | 435/6 |
| 6,153,421 A | 11/2000 | Yanagi et al. | 435/235.1 |
| 2003/0134297 A1 | 7/2003 | Olson et al. | 436/6 |
| 2003/0232745 A1 | 12/2003 | Olson et al. | 514/2 |

FOREIGN PATENT DOCUMENTS

| | | |
|---|---|---|
| EP | 388232 A1 * | 9/1990 |
| EP | 1178116 A1 | 2/2002 |
| WO | WO 99/04008 | 1/1999 |

OTHER PUBLICATIONS

"Prevention". Dictionary of Cancer Terms. National Cancer Institute. internet document <<http://www.cancer.gov/templates/db_alpha.aspx?print=1&cdrid=439419>>, accessed Nov. 25, 2007, 1 page.*

Robert F. Garry, et al., "Proteomics Computational Analysis Suggest that Hepatitis C Virus E1 and Pestivirus E2 Envelope Glycoproteins and Truncated Class II Fusion Proteins," *Virology*, 307:255-265 (2003).

Hoffman-LaRoche and Trimeris, "Roche and Trimeris Announce 24-Week Results from Second Pivotal Study of HIV Inhibitor T-20", trimeris.com/news/pr/2002/020516.html.

Richard J. Kuhn et al., "Structure of Dengue Virus: Implications for Flavivirus Organization, Maturation, and Fusion", *Cell*, 108:717-725 (2002).

R.J. Medinas et al., "C-Terminal gp40 Peptide Analogs Inhibit Feline Immunodeficiency Virus: Cell Fusion and Virus Spread", *Journal of Virology*, 76(18)9079-9086 (2002).

Julien Lescar, et al., "The Fusion Glycoprotein Shell of Semliki Forest Virus: An Icosahedral Assembly Primed for Fusogenic Activation at Endosomal pH",*Cell*, 105:137-148 (2001).

Tatiana Suárez, "Membrane Interface-Interacting Sequences within the Ectodomain of the Human Immunodeficiency Virus Type 1 Envelope Glycoprotein: Putative Role During Viral Fusion", *Journal of Virology*, 74(17):8038-8047 (2000).

M. Flint et al., "The Role of Hepatitis C Virus Glycoproteins in Infection", *Medical Virology*, 10:101-117 (2000).

Mike Flint et al., "Functional Analysis of Cell Surface-Expressed Hepatitis C Virus E2 Glycoprotein", *Journal of Virology*, 73(8):6782-6790 (1999).

Winfried Weissenhorn et al., "Crystal Structure of the Ebola Virus Membrane Fusion Subunit, GP2, from the Envelope Glycoprotein Ectodomain", *Molecular Cell*, 2:605-616 (1998).

Carl Wild et al., "A Synthetic Peptide from HIV-1 gp41 Is a Potent Inhibitor of Virus-Mediated Cell-Cell Fusion", *Aids Research and Human Retroviruses*, 9(11):1051-1053 (1993).

Carl Wild et al., "Peptides Corresponding to a Predictive α-Helical Domain of Human Immunodeficiency Virus Type 1 gp41 are Potent Inhibitors of Virus Infection", *Proc. Natl. Acad. Sci. USA*, 91:9770-9774 (1994).

William R. Gallaher, "Detection of a Fusion Peptide Sequence in the Transmembrane Protein of Human Immunodeficiency Virus", *Cell*, 50:327-328 (1987).

* cited by examiner

*Primary Examiner*—Andrew D. Kosar
(74) *Attorney, Agent, or Firm*—Howrey LLP

(57) ABSTRACT

The present invention relates to methods that employ peptides or peptide derivatives to inhibit hepatitis C virus infection. The present invention is based in part on the discovery that E2 envelope glycoprotein of hepatitis C virus has previously undescribed domains that are important for interactions with cellular or viral proteins that are necessary for early steps in HCV infection. The present invention provides peptides and methods of treatment and prophylaxis of diseases induced by hepatitis C virus and related viruses.

14 Claims, 4 Drawing Sheets

```
H77  ETHVTGGSAG RTTAGLVGLL TPGAKQNIQL INTNGSWHIN STALNCNESL NTGWLAGLFY
J4   ETHTTGRVAG HTTSGFTSLF SSGASQKIQL VNTNGSWHIN RTALNCNDSL QTGFFAALFY

H77  QHKFNSSGCP ERLASCRRLT DFAQGWGPIS YANGSGLDER PYCWHYPPRP CGIVPAKSVC
J4   AHKFNSSGCP ERMASCRPID WFAQGWGPIT YTKPNSSDQR PYCWHYAPRP CGVVPASQVC

H77  GPVYCFTPSP VVVGTTDRSG APTYSWGAND TDVFVLNNTR PPLGNWFGCT WMNSTGFTKV
J4   GPVYCFTPSP VVVGTTDRSG VPTYSWGENE TDVMLLNNTR PPQGNWFGCT WMNSTGFTKT

H77  CGAPPCVIGG VGNNTLLCPT DCFRKHPEAT YSRCGSGPWI TPRCMVDYPY RLWHYPCTIN
J4   CGGPPCNIGG VGNRTLICPT DCFRKHPEAT YTKCGSGPWL TPRCLVDYPY RLWHYPCTLN

H77  YTIFKVRMYV GGVEHRLEAA CNWTRGERCD LEDRDRSELS PLLLSTTQWQ VLPCSFTTLP
J4   FSIFKVRMYV GGVEHRLNAA CNTRGERCN LEDRDRSELS PLLLSTTEWQ ILPCAFTTLP

H77  ALSTGLIHLH QNIVDVQYLY GVGSSIASWA IKWEYVVLLF LLLADARVCS CLWMMLLISQ
J4   ALSTGLIHLH QNIVDVQYLY GVGSAFVSFA IKWEYILLLF LLLADARVCA CLWMMLLIAQ
```

FIGURE 1

Hepatitis C virus
envelope protein 2 (E2)

FIGURE 3

INHIBITORS OF HEPATITIS C VIRUS

CROSS-REFERENCE TO RELATED APPLICATION

This application claims priority to U.S. provisional patent application Ser. No. 60/614,280, entitled "Inhibitors of Hepatitis C Virus," by Robert F. Garry, Jr. and Jane A. McKeating, filed Sep. 29, 2004, which is incorporated by reference herein in its entirety.

FIELD OF THE INVENTION

The present invention relates to peptides and methods of inhibiting virus-cell binding and entry of hepatitis C virus. Specific embodiments of the invention are drawn to the inhibition of infection by hepatitis C virus (HCV).

BACKGROUND OF THE INVENTION

Viruses must infect host cells to replicate, produce a spreading infection, and cause disease. Infection by enveloped viruses requires binding of the virion to one or more structures on the cell surface (Flint and McKeating, 2000). The initial step may be a low affinity non-specific binding (Barth et al., 2003). Subsequently, the virus binds with high affinity to primary receptors, and then in some cases to secondary receptors or co-receptors (Bartosch et al., 2003; Hsu et al., 2003; Roccasecca et al., 2003; Cormier et al., 2003; Pohlmann et al., 2003; Zhang et al., 2004). The cell surface binding steps can be associated with a variety of structural rearrangements of the virion surface proteins and changes in protein-protein interactions between the viral surface proteins (Jardetsky and Lamb, 2004; Modis et al., 2004; Bressanelli et al., 2004; Gibbons et al, 2004). The latter steps can expose the fusion peptide, a hydrophobic domain of a viral glycoprotein that is able to interact with cell membranes (Flint et al., 1999; Allison et al., 2001). In some cases, the binding of the virus to the cell surface receptors triggers uptake of the virus through endocytic, or similar vesicular pathways (Garry and Dash, 2003; Jardetsky and Lamb, 2004). Exposure to more acidic conditions in the vesicles can trigger conformational changes in the viral surface proteins, including those that expose the fusion peptide (Kuhn et al., 2002; Lescar et al., 2001). For most viruses, binding to the cellular receptor is primarily the function of one viral surface protein, whereas fusion of the viral and cellular membranes is primarily the function of another viral surface protein. An example of a virus with separate receptor binding and fusion protein is HIV. The receptor binding protein of HIV is the surface glycoprotein (SU; gp120) and the fusion protein is the transmembrane glycoprotein (TM;gp41) (Kwong et al., 1998; Gallaher et al., 1987; 1989). Most viruses with class I fusion proteins in which the fusion peptide is located at or near the amino terminus, for example retroviruses, orthomyxoviruses, paramyxoviruses arenaviruses and coronaviruses, use one protein for receptor binding and another for fusion (Wilson et al., 1981; Gallaher et al, 1996; 2001). Alphaviruses, which have a class II fusion protein with an internal fusion peptide, also use one protein principally for receptor binding and another for fusion of the viral and cellular membranes (Straus and Straus, 1994). The envelope (E) protein encoded by members of the flavivirus genus of the Flaviviridae, has an internal fusion peptide, but serves both receptor binding and fusion function (Allison et al., 2001).

Hepatitis C virus encodes two envelope glycoproteins, E1 (gp35) and E2 (gp70), both with C-terminal transmembrane anchor domains (Flint and McKeating, 2000). E2 interacts with several cell surface proteins (CD81, SR-BI and L-SIGN) suggesting that it is the receptor binding protein of HCV (McKeating, 2004). The function of E1 is less clear and may act to chaperone E2 (Flint et al., 1999; Garry and Dash, 2003). Synthetic peptides corresponding to hepatitis C virus E2 can block infection mediated by hepatitis C virus. Structural determinations of the hepatitis C virus E2 allow the identification of several heretofore unknown features of hepatitis C virus E2 for drug and vaccine development.

The Flavivirus family includes a variety of important human and animal pathogens. Hepatitis C virus (HCV) is the leading viral cause of chronic hepatitis, cirrhosis, liver failure, and hepatocellular carcinoma (Poynard et al., 2003). In the United States alone, an estimated 4 million people are infected with HCV. This is approximately four times the number infected by HIV. Each year in the US, 30-50,000 new HCV infections occur, and about 15-20,000 people die. Moreover, these numbers are expected to increase dramatically given that a substantial portion of HCV infected individuals show little or no response to the only currently approved therapeutics (i.e. treatment with interferons and/or ribavirin). HCV infection is spread primarily through needle sharing among drug users, although there is some risk from accidental needle sticks, blood products before 1992, chronic blood dialysis, and frequent sexual contact. Current treatments for HCV using ribavirin and interferon cost ~$8,000 to $20,000 per year, and are only partially successful in about half of patients treated. Overall, about 80% of HCV carriers suffer chronic liver inflammation and cirrhosis, of these 25% will develop end stage liver disease or hepatocellular carcinoma (HCC) (Colombo, 2000). End stage HCV disease is the most frequent indication for liver transplants and this costs $250,000 to $300,000. Better drugs to treat HCV infection and an effective vaccine to prevent HCV infection are urgently needed.

SUMMARY OF THE INVENTION

The present invention relates to the compositions comprising peptides or peptide derivatives and methods that employ these compositions to treat, prevent or inhibit infection by hepatitis C virus (HCV) and related viruses. The present invention is made possible by the inventors' discovery that that HCV encoded E2 glycoprotein (and the analog(s) from related viruses) has previously undescribed domains that are important for interaction(s) and rearrangements of E2 with E2 and/or E1, for high affinity interactions with cellular receptors, or for E2 and E1-E2 protein-protein interactions that occur prior to virion:cell membrane fusion. Thus, the present invention provides peptides and methods for treatment and prophylaxis of diseases induced by HCV and related viruses.

The instant invention teaches that HCV envelope glycoprotein E2 has several domains that can be targeted by synthetic peptides to block infection and pathogenesis. The regions of HCV E2 are important for the binding of HCV to its low or high affinity cellular receptors, for rearrangements of E2 or for protein-protein interactions of E2 that occur prior to virion:cell membrane fusion. This invention also teaches and provides synthetic peptides that can inhibit receptor binding and other pre-fusion steps mediated by HCV E2.

Features of hepatitis C virus envelope glycoprotein 2 identified herein provide surprising guidance for the development of vaccines and/or drugs to prevent or treat hepatitis C virus infections. According to one embodiment of the invention, the target for the peptides is E2, the receptor binding protein of HCV. Although proteins, such as soluble CD4, chemokines and antibodies have been developed that block infection by targeting virion receptor binding interactions, peptide mimics of viral surface proteins that block this or other pre-fusion steps have not be described. Prior to the availability of X-ray structural data (Qureshi et al., 1990; Wild, et al., 1993; 1994), several potent HIV-1 inhibitors were developed based on the Gallaher HIV-1 TM fusion protein model (Gallaher et al., 1989). One of these inhibitors, FUZEON® (aka enfuvirtide, DP178; T20) peptide has been shown to substantially reduce HIV-1 load in AIDS patients in clinical trials (Lalezari, et al., 2003). The peptide drugs, which are the subject of the instant invention, were also developed without benefit of X-ray structural data. FUZEON® targets HIV fusion protein and the steps in HIV entry involving fusion between the viral and cellular membrane. Certain hepatitis C virus E2 inhibitory peptides target different steps in the viral replication cycle than are targeted by FUZEON® and other known viral peptide inhibitors. E2-based peptide drugs should be relatively easy to develop, based on our identification of E2 domains that can be targeted by synthetic peptides to block infection and pathogenesis. Once an effective peptide inhibitor is described a non-peptide drug can be developed.

More specifically, the present invention provides for methods of inhibiting viral infection and pathogenesis by hepatitis C virus. The invention is related to the discovery, as described herein, of hepatitis C virus E2 domains that can be targeted by synthetic peptides to block infection and pathogenesis. Various embodiments of the invention provide methods that employ peptides or peptide derivatives to inhibit hepatitis C virus receptor binding, E2 structural rearrangements or protein-protein interactions, or other pre-fusion steps. The present invention provides for methods of treatment and prophylaxis of diseases induced by hepatitis C virus.

Various embodiments of the instant invention provide for pharmaceutical compositions comprising one or more peptides selected from one or more of the following groups.

A) Peptides having the sequence of any of SEQ ID NO:1 to SEQ ID NO:6;

B) Peptides homologous to any one of SEQ ID NO:1 to SEQ ID NO:6, except that they are from a different strain of hepatitis C virus.

C) Peptides homologous to any one of SEQ ID NO:1 to SEQ ID NO:6, except that they are from hepatitis GB virus.

D) Peptides that are functionally equivalent to any one of SEQ ID NO:1 to SEQ ID NO:6, wherein the functionally equivalent peptide is identical to at least one of SEQ ID NO:1 to SEQ ID NO:6 except that one or more amino acid residues has been substituted with a homologous amino acid, resulting in a functionally silent change, or one or more amino acids has been deleted. An homologous amino acid is an amino acid with chemical or functional similarity to another amino acid. Sets of homologous amino acids are: nonpolar amino acids: alanine, leucine, isoleucine, valine, proline, phenylalanine, tryptophan and methionine; polar neutral amino acids: glycine, serine, threonine, cysteine, tyrosine, asparagine, and glutamine; hydrophobic amino acids: leucine, isoleucine, valine, methionine, alanine, phenylalanine; basic amino acids: lysine, arginine, histidine; acidic amino acids and their amides: aspartic acid, asparginine; glutamic acid, glutamine; aromatic amino acids: tyrosine, tryptophan, phenylalanine, histidine; amino acid alcohols: serine, threonine; and small amino acids: glycine, proline. For example, and not by way of limitation, such peptides may also comprise one or more D-amino acids.

Various aspects of this embodiment of the invention provide for compositions that comprise one or more peptides having one or more of the following traits:

A) Peptides having the amino acid sequence of one or more of SEQ ID NO:1 to SEQ ID NO:42, wherein the N-terminal end of the peptide terminates in an amino group and the C-terminal end of the peptide terminates in a carboxyl group.

B) Peptides having the sequence of any of SEQ ID NO:1 to SEQ ID NO:42, wherein the peptide's N-terminal end does not terminate in an amino group and/or the peptide's C-terminal end does not a terminate in carboxyl group, wherein the peptide's N-terminal end terminates in a moiety selected from the group consisting of: an acetyl group, a hydrophobic group, carbobenzoxyl group, dansyl group, a t-butyloxycarbonyl group, or a macromolecular carrier group, and/or wherein the peptide's C-terminal end terminates in a moiety selected from the group consisting of an amido group, a hydrophobic group, t-butyloxycarbonyl group or a macromolecular group.

C) Peptides having the sequence of any of SEQ ID NO:1 to SEQ ID NO:42 except that at least one bond linking adjacent amino acid residues is a non-peptide bond.

D) Peptides having the sequence of any of SEQ ID NO:1 to SEQ ID NO:42, except that at least one amino acid residue is in the D-isomer configuration.

E) Peptides as in groups "A)" or "B)" except that at least one amino acid has been substituted for by a different amino acid (whether a conservative or non-conservative change). Preferably the peptide comprises 1, 2, 3, 4, 5, or more conservative or non-conservative changes. As used herein the term "a conservative change" is preferably defined as substitution in the peptide sequence of an amino acid by a homologous amino acids (for example, a substitution of a leucine for another hydrophobic amino acid such as isoleucine). A non-conservative change is defined as substitution in the peptide sequence of an amino acid by a non-homologous amino acids (for example, a substitution of the acidic aspartic acid for the basic amino acid arginine).

F) Peptides that are a functional fragment of a peptide as set out in any of groups "A)" to "E)", above, where the peptides have at least 3 contiguous nucleotides of any one of SEQ ID NO:1 to SEQ ID NO:42. As used herein, the term "a functional fragment of an inhibitory peptide" is preferably defined is a peptide with a shorter sequence consisting of a subset of the amino acids of the inhibitory peptide, which fragment retains the inhibitory properties. For example, "DEFGHKL" could represent a functional fragment of inhibitory peptide "ABCDEFGHIJKLMNOP" if it was inhibitory. And, G) Peptides that combine the modification of two or more of part "A"-"F". For example, a peptide that comprises non-peptide bonds linking two or more of the constituent amino acid residues and has an N-terminal moiety that is not an amino group.

The instant invention also provides for substantially purified antibodies that specifically react with one or more of the peptides described above.

The instant invention also provides for methods for treating or preventing HCV infections where the method comprises administering one or more of the peptides and/or antibodies as described above.

The instant invention also provides for methods for treating or preventing hepatitis C virus infections where the method comprises administering to a patient in need of such treatment a composition comprising one or more of the peptides and/or antibodies as described above in combination with peptides and/or antibodies or peptides targeting the fusion step mediated at least in part by hepatitis C virus envelope protein 1 as described in international application PCT/US2003/035666 which is herein incorporated by reference. The HCV E2 and E1 peptides and/or antibodies may work synergistically (i.e. they may be active at lower concentrations in combination that when used separately) or they may act in a complimentary or additive fashion.

Abbreviations
HCV—hepatitis C virus
HSA—human serum albumen

BRIEF DESCRIPTION OF THE DRAWINGS

FIG. 1: Alignment of protein E2 peptide sequences from two strains of hepatitis C virus showing locations of active peptides. E2 sequences from H77, a genotype 1a strain of HCV (SEQ ID NO:139), and J4, a genotype 1b strain of HCV (SEQ ID NO:140), were aligned. A ":" indicates an identical amino acid and a"." indicates a chemically similar amino acid in the two sequences. Bars above or below the amino acid sequences indicate the locations of peptides, numbered as in Tables 7 and 8, that inhibit infection by an HCV pseudotype.

FIG. 3: Structure of hepacivirus E2 glycoprotein showing location of active peptides, numbered as in Tables 7 and 8. A two dimensional model of HCV envelope protein 2 (SEQ ID NO:141) was constructed using a proteomics computational tool and comparisons to receptor binding proteins of other RNA viruses. Sequences that resulted in greater than 70% reduction in HCV pseudotype infectivity are indicated.

DETAILED DESCRIPTION OF THE INVENTION

Figure 2:
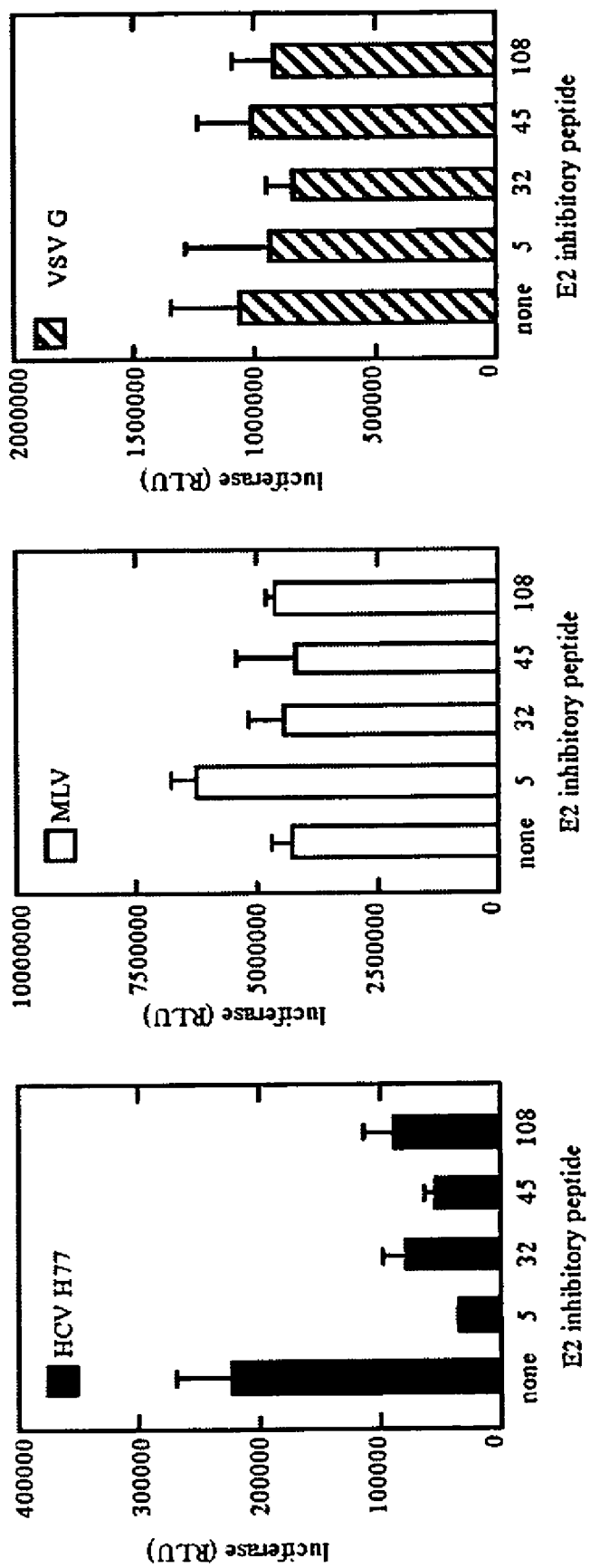
FIG. 2. Specificity of HCV E2 inhibitory peptides. E2 peptides, numbered as in Tables 7 and 8, were added to pseudotypes containing the core proteins of HIV and HCV E1, E2, murine leukemia virus surface and transmembrane glycoproteins (SU and TM), or vesicular stomatitis virus glycoprotein (G). Supernatants were also treated with DMSO vehicle alone or with a Mab (monoclonal antibody) to HCV E2 known to neutralize pseudotype infectivity. Peptide treated and control pseudotypes were added to cells, which were incubated at 37° C. for 72 h. Cell lysates were then tested for luciferase activity as described (Hsu et al., 2003).

The present invention relates to compositions for and methods of preventing, treating, or inhibiting Flavivirus infection. The currently disclosed compositions and methods are theorized to operate by inhibiting the fusion between the virion envelope and a cell membrane, the process that delivers the viral genome into the cell cytoplasm.

Various embodiments of the invention, provide the identification and sequence of HCV inhibitory peptides representing specific portions of the HCV E2 glycoprotein. These inhibitory peptides proteins are believed to function by interfering with and blocking receptor binding. These peptides include those represented by SEQ ID NOs 1-42 and derivatives thereof as described below.

In particular aspects of this embodiment of the invention compositions comprising peptides corresponding to the HCV envelope glycoprotein 2 are useful at a broad range of doses (as shown in Example 1 these peptides are effective at inhibiting HCV fusion with the cells).

For purposes of clarity of disclosure, and not by way of limitation, the description of the present invention will be divided into the following subsections:
(i) Peptides of the invention
(ii) Utilities of the invention (including compositions and methods for employing the peptides)

TABLE 1

HCV E2 inhibitory peptide 1

| PROTEIN | SEQUENCE* | |
|---|---|---|
| HCV E2 a | X-LVGLLTPGAKQNIQLINTNGSWHINS-Z | (SEQ ID NO:1) |
| HCV E2 b | X-FTSLFSSGASQKIQLVNTNGSWHINR-Z | (SEQ ID NO:7) |
| HCV E2 a | X-LAGLFTSGAKQNIQLINTNGSWHINR-Z | (SEQ ID NO:8) |
| HCV E2 b | X-FTSFFTRGPSQNLQLVNSNGSWHINS-Z | (SEQ ID NO:9) |
| HCV E2 a | X-LANLFSSGSKQNLQLINSNGSWHINR-Z | (SEQ ID NO:10) |
| HCV E2 a | X-LTSFFNPGPQRQLQFVNTNGSWHINS-Z | (SEQ ID NO:11) |
| HCV E2 a | X-FASLLTPGAKQNIQLINTNGSWHINR-Z | (SEQ ID NO:12) |

TABLE 2

HCV E2 inhibitory peptide 2

| PROTEIN | SEQUENCE* | |
|---|---|---|
| HCV E2 1a | X-CNESLNTGWLAGLFYQH-Z | (SEQ ID NO:2) |
| HCV E2 1b | X-CNDSLHTGFLAALFYTH-Z | (SEQ ID NO:13) |
| HCV E2 2a | X-CNDSLNTGFIASLFYTY-Z | (SEQ ID NO:14) |
| HCV E2 3b | X-CNDSLNTGFIAGLFYYH-Z | (SEQ ID NO:15) |
| HCV E2 4a | X-CNDSLNTGFLASLFYTH-Z | (SEQ ID NO:16) |
| HCV E2 5a | X-CNDSLQTGFIAGLMYAH-Z | (SEQ ID NO:17) |
| HCV E2 6a | X-CNDSLQTGFLASLFYTH-Z | (SEQ ID NO:18) |

TABLE 3

HCV E2 inhibitory peptide 3

| PROTEIN | SEQUENCE* | |
|---|---|---|
| HCV E2 1a | X-YSWGANDTDVFVLNNTRPPLGNWFGCTWMNSTGF-Z | (SEQ ID NO:3) |
| HCV E2 1b | X-YSWGENETDVMLLNNTRPPQGNWFGCTWMNSTGF-Z | (SEQ ID NO:19) |
| HCV E2 2a | X-YTWGENETDVFILNSTRPPGGSWFGCTWMNSTGF-Z | (SEQ ID NO:20) |
| HCV E2 3b | X-YRFGVNESDVFLLTSLRPPQGRWFGCVWMNSTGF-Z | (SEQ ID NO:21) |
| HCV E2 4a | X-YTWGENETDVFLLNSTRPPHGAWFGCVWMNSTGF-Z | (SEQ ID NO:22) |
| HCV E2 5a | X-YNWGSNETDILLLNNIRPPAGNWFGCTWMNSTGF-Z | (SEQ ID NO:23) |
| HCV E2 6a | X-YTWGENETDVFMLESLRPPTGGWFGCTWMNSTGF-Z | (SEQ ID NO:24) |

TABLE 4

HCV E2 inhibitory peptide 4

| PROTEIN | SEQUENCE* | |
|---|---|---|
| HCV E2 1a | X-DYPYRLWHYPCTINYTIFKVRMYVGGV-Z | (SEQ ID NO:4) |
| HCV E2 1b | X-DYPYRLWHYPCTLNFSIFKVRMYVGGV-Z | (SEQ ID NO:25) |
| HCV E2 2a | X-DYPYRLWHYPCTINYTIFKIRMYVGGV-Z | (SEQ ID NO:26) |
| HCV E2 3b | X-DYPYRLWHYPCTVNFSIFKVRMFVGGH-Z | (SEQ ID NO:27) |
| HCV E2 4a | X-DYPYRLWHFPCTANFSVFNIRTFVGGI-Z | (SEQ ID NO:28) |
| HCV E2 5a | X-HYPYRLWHYPCTVNYTIFKVRMFIGGL-Z | (SEQ ID NO:29) |
| HCV E2 6a | X-DYAYRLWHYPCTVNFTLHKVRMFVGGT-Z | (SEQ ID NO:30) |

TABLE 5

HCV E2 inhibitory peptide 5

| PROTEIN | SEQUENCE* | |
|---|---|---|
| HCV E2 1a | X-ALSTGLIHLHQNIVDVQYLYGVGSSIASWAIKWEY-Z | (SEQ ID NO:5) |
| HCV E2 1b | X-ALSTGLIHLHQNIVDVQYLYGVGSAFVSFAIKWEY-Z | (SEQ ID NO:31) |
| HCV E2 2a | X-ALSTGLLHLHQNIVDVQYMYGLSPALTKYIVRWEW-Z | (SEQ ID NO:32) |
| HCV E2 3b | X-RLSTGLIHLHQNIVDVQYLYGVGSAVVGWALKWEF-Z | (SEQ ID NO:33) |
| HCV E2 4a | X-ALSTGLIHLHQNIVDVQYLYGVGSAVVSWALKWEY-Z | (SEQ ID NO:34) |
| HCV E2 5a | X-ALSTGLIHLHQNIVDTQYLYGLSSSIVSWAVKWEY-Z | (SEQ ID NO:35) |
| HCV E2 6a | X-ALSTGLIHLHQNIVDVQYLYGVSTNVTSWVVKWEY-Z | (SEQ ID NO:36) |

TABLE 6

HCV E2 inhibitory peptide 6

| PROTEIN | SEQUENCE* | |
|---|---|---|
| HCV E2 1a | X-VVLLFLLLADARVCSCLWMMLLISQAEA-Z | (SEQ ID NO:6) |
| HCV E2 1b | X-ILLLFLLLADARVCACLWMMLLIAQAEA-Z | (SEQ ID NO:37) |
| HCV E2 2a | X-VVLLFLLLADARVCACLWMLILLGQAEA-Z | (SEQ ID NO:38) |
| HCV E2 3b | X-VVLVFLLLADARVCVALWMMLLISQAEA-Z | (SEQ ID NO:39) |
| HCV E2 4a | X-VVLAFLLLADARVSAYLWMMFMVSQVEA-Z | (SEQ ID NO:40) |
| HCV E2 5a | X-IMLVFLLLADARICTCLLILLLICQAEA-Z | (SEQ ID NO:41) |
| HCV E2 6a | X-IVLMFLVLADARICTCLWLMLLISTVEA-Z | (SEQ ID NO:42) |

* In tables 1-6 the "X" and "Z" on each peptide respectively represent the N- and C-terminal moiety. As described above the N-terminal moiety may be either an amino group or it may be selected from the group consisting of an acetyl group, a hydrophobic group, carbobenzoxyl group, dansyl group, a t-butyloxycarbonyl group, or a macromolecular carrier group and/or the peptide's C-terminal moiety may be a carboxy group or it may be a moiety selected from the group consisting of: an amido group, a hydrophobic group, t-butyloxycarbonyl group or a macromolecular group.

Peptides of the Invention

Any peptide or protein which inhibits the fusion between the Hepatitis C virus E2 virion envelope and a cell membrane, including those of Hepatitis C virus E2 which infect human as well as nonhuman hosts, may be used according to the invention. In various embodiments of the invention, these inhibitors may include, but are not limited to peptides related to several membrane-interactive domains of Hepatitis C virus E2.

Hepatitis C virus E2 inhibitory peptides are, according to the instant invention, identical or homologous to the amino acid sequences As used herein the term "conservative substitution" preferably refers to substitution in the peptide sequence of an amino acid by a homologous amino acid.

As used herein the term "peptide derivative" preferably refers to: a peptide modified by the addition of one or more groups, including, but not limited to a carbobenzoxyl group, a dansyl group, t-butyloxycarbonyl group, a lipid conjugate, a polyethylene glycol group, or a carbohydrate As used herein the term "similar peptides" refers to those peptides having at least 70% identical or chemically similar amino acids. More preferably, it refers to peptides having 75%, 80%, 85%, 90%, 95%, 96%, 97%, 98% or greater identical and/or chemically equivalent amino acid resides.

As used herein the terms "portion thereof" refers to the peptide resulting from the removal of from one or more amino acids from either or both ends of the listed peptide, i.e. a truncated peptide. The number of amino acids removed may vary from 1-10 so long as the remaining fragment is "functional". As defined herein the term "functional fragment" refers to a fragment capable of inhibiting virus:cell fusion, inhibiting viral infectivity, capable of eliciting an antibody capable of recognizing and specifically binding to non-truncated peptide and/or interfering with hepatitis C virus envelope protein 2-mediated cell infection.

According to the instant invention peptides related to the Hepatitis C virus E2 inhibitory peptides (E2IP) preferably comprise at least three contiguous residues of the E2IP peptides, or a homologous peptide, more preferably they comprise 4, 5, 6, or 7 contiguous residues. Even more preferably they comprise at least 8, 9, 10, 11, 12, 13, 14, 15, 16, 17, 18, 19, 20, 21, 22, 23, 24, 25, 26, 27, 28, 29, or 30 or more contiguous residues (up to the maximum number of residues in the peptide), and most preferably all residues of these sequences. As used herein the term Hepatitis C virus E2 inhibitory peptides preferably means peptides having a sequence identical to the corresponding portion of the Hepatitis C virus E2 inhibitory protein and peptides in which one or more amino acids are substituted by functionally equivalent amino acids (see infra). The term also refers to derivatives of these peptides, including but not limited to benzylated derivatives, glycosylated derivatives, and peptides which include enantiomers of naturally occurring amino acids. In other embodiments of the invention, the Hepatitis C virus E2 inhibitory peptides, related peptides or derivatives are linked to a carrier molecule such as a protein. Proteins contemplated as being useful according to this embodiment of the invention, include but are not limited to, (human serum albumen). Hepatitis C virus E2 inhibitory peptide-related peptides comprising additional amino acids are also contemplated as useful according to the invention.

Peptides may be produced from naturally occurring or recombinant viral proteins, or may be produced using standard recombinant DNA techniques (e.g. the expression of peptide by a microorganism which contains recombinant nucleic acid molecule encoding the desired peptide, under the control of a suitable transcriptional promoter, and the harvesting of desired peptide from said microorganism). Preferably, the peptides of the invention may be synthesized using any methodology known in the art, including but not limited to, Merrifield solid phase synthesis (Clark-Lewis et al., 1986).

The E2IP, or fragments or derivatives thereof, of the invention include, but are not limited to, those containing, as a primary amino acid sequences the amino acid sequence hepatitis C virus E2 Inhibitory peptide 1: LVGLLTPGAKQ-NIQLINTNGSWHINS SEQ ID NO:1; HCV E2 Inhibitory peptide 2 CNESLNTGWLAGLFYQH SEQ ID NO:2; HCV E2 Inhibitory peptide 3, YSWGANDTDVFVLNNTRP-PLGNWFGCTWMNSTGF SEQ ID NO:3; or HCV E2 Inhibitory peptide 4, DYPYRLWHYPCTINY-TIFKVRMYVGGV SEQ ID NO:4; HCV E2 Inhibitory peptide 5, X-ALSTGLIHLHQNIVDVQYLYGVGS-SIASWAIKWEY SEQ ID NO:5; E2 Inhibitory peptide 6, VVLLFLLLADARVCSCLWMMLLISQAEA, SEQ ID NO:6 or a functional portion or functional portions thereof.

Also contemplated are altered sequences analogous to any of SEQ ID NOs 1-42; more preferably analogous to any of SEQ ID NO:1-6 (i.e. altered from any of the sequences referred to herein) in which functionally equivalent amino acid residues are substituted for residues within the sequence, resulting in a functionally silent change. For example, one or more amino acid residues within the sequence can be substituted by replacing the original amino acid with another amino acid, of a similar polarity, that acts as a functional equivalent, resulting in a functionally silent alteration. Substitutes for an amino acid within the sequence may be selected from other members of the class to which the amino acid belongs. For example, classes of homologous amino acids are: nonpolar amino acids: alanine, leucine, isoleucine, valine, proline, phenylalanine, tryptophan and methionine, polar neutral amino acids: glycine, serine, threonine, cysteine, tyrosine, asparagine, and glutamine, hydrophobic amino acids: leucine, isoleucine, valine, methionine, alanine, phenylalanine; basic amino acids: lysine, arginine, histidine; acidic amino acids and their amides: aspartic acid, asparginine; glutamic acid, glutamine; aromatic amino acids, tyrosine, tryptophan, phenylalanine, histidine; amino acid alcohols: serine, threonine and small amino acids: glycine, proline. For example, and not by way of limitation, such peptides may also comprise one or more D-amino acids. Furthermore, in any of the embodiments of the instant invention the peptide may comprise an inefficient carrier protein, or no carrier protein at all.

Further, as noted supra, in any embodiment of the invention the peptide's N-terminal moiety may be either an amino group (as is typically found in naturally occurring proteins/peptides) or it may be selected from the group consisting of an acetyl group, a hydrophobic group, carbobenzoxyl group, dansyl group, a t-butyloxycarbonyl group, or a macromolecular carrier group and/or the peptide's C-terminal moiety may be a carboxy group (as is typically found in naturally occurring proteins/peptides) or it may be a moiety selected from the group consisting of: an amido group, a hydrophobic group, t-butyloxycarbonyl group or a macromolecular group.

Utility of the Invention

The hepatitis C virus E2 inhibitory peptides of the instant invention may be utilized to inhibit hepatitis C virus infection and may, accordingly, be used in the treatment: of hepatitis C virus infection and also in prophylaxis against hepatitis C virus infection. The peptides of the invention may be administered to patients in any sterile, biocompatible pharmaceutical carrier, including, but not limited to, saline, buffered saline, dextrose, and water. Methods for administering peptides to patients are well known to those of skill in the art; they include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection.

The instant invention provides for compositions, especially pharmaceutical compositions, comprising hepatitis C virus E2 inhibitory peptides, peptide fragments, or derivatives (as described supra) administered via liposomes, microparticles, or microcapsules. Various embodiments of the invention, contemplate the use of such compositions to achieve sustained release of hepatitis C virus E2 inhibitory peptides. Other embodiments contemplate the administration of the FIP or derivatives thereof, linked to a molecular carrier (e.g. HSA).

Various embodiments of the instant invention provide for administration of the hepatitis C virus E2 inhibitory peptides and/or antibodies specific for these peptides to human subjects who suffer from hepatitis C virus infection. In any embodiment the peptides and/or antibodies are typically substantially purified. As used herein the term "substantially purified" refers to a peptide, peptide analog, or antibody that is greater than about 80% pure. More preferably, "substantially purified" refers to a peptide, peptide analog, or antibody that is greater than about 90% or greater than about 95% pure. Most preferably it refers to a peptide, peptide analog, or antibody that is greater than 99% pure. Functionally, "substantially purified" means that it is free from contaminants to a degree that that makes it suitable for the purposes provided herein. Other embodiments provide for the prophylactic administration of the peptides to those at risk for hepatitis C virus infection.

Other embodiments of the instant invention provide for methods for identifying the structure of truncated hepatitis C virus E2 proteins which involved hepatitis C virus receptor binding, E2 structural rearrangements or protein-protein interactions, or other, pre-fusion steps by members of the Flaviviridae family and for the structures themselves.

Other embodiments of the invention provide for a peptide having a formula selected from one or more of the following.

The E2IP, or fragments or derivatives thereof, of the invention include, but are not limited to, those containing, as a primary amino acid sequences the amino acid sequence hepatitis C virus E2 Inhibitory peptide 1: LVGLLTPGAKQ-NIQLINTNGSWHINS (SEQ ID NO:1); HCV E2 Inhibitory peptide 2: CNESLNTGWLAGLFYQH (SEQ ID NO:2); HCV E2 Inhibitory peptide 3: YSWGANDTDVFVLNNTR-PPLGNWFGCTWMNSTGF (SEQ ID NO:3); or HCV E2 Inhibitory peptide 4: X-DYPYRLWHYPCTINY-TIFKVRMYVGGV (SEQ ID NO:4); HCV E2 Inhibitory peptide 5 ALSTGLIHLHQNIVDVQYLYGVGS-SIASWAIKWEY (SEQ ID NO:5); HCV inhibitory peptide 6: VVLLFLLLADARVCSCLWMMLLISQAEA (SEQ ID NO:6); or a functional portion or functional portions thereof of any of these peptides.

According to various embodiments of the instant invention, any of the peptides described herein may comprise an amino group at the amino-terminal end or may be modified to comprise any of the following: an acetyl group, a hydrophobic group or a macromolecular carrier group. Similarly, the carboxy-terminus of any of the peptides may comprise a carboxyl group or may be modified to comprise any of the following groups: an amido group a hydrophobic group or a macromolecular carrier group. In other aspects of this embodiment of the invention, the amino terminal group is a hydrophobic group, a carbobenzoxyl group, a dansyl group, t-butyloxycarbonyl group, a lipid conjugate, a polyethylene glycol group, or a carbohydrate. In any aspect of this embodiment the carboxy terminal group may be a t-butyloxycarbonyl group, a lipid conjugate, a polyethylene glycol group, or a carbohydrate.

Moreover, aspects of this embodiment also include peptides wherein at least one bond linking adjacent amino acids residues is a non-peptide bond. In particularly preferred aspects of this embodiment the non-peptide bond is an imido, ester, hydrazine, semicarbazoide or azo bond.

Other aspects of this embodiment provide for peptides wherein at least one amino acid is a D-isomer amino acid.

Additional aspects of this embodiment of the invention provide for peptides wherein compromising at least one amino acid substitution has been made so that a first amino acid residue is substituted for a second, different amino acid residue. These substitutions may be conservative or non-conservative, as long as the peptide is still functional according to the instant invention.

Other aspects of this embodiment of the invention provide for peptides wherein at least one amino acid has been deleted. As noted, supra, the peptides according to this embodiment of the invention must comprise at least 3 contiguous amino acids of one of the SEQ ID NOs indicated above and must be a functional segment.

Other embodiments of the invention provide for compositions comprising one or more of the peptides and/or antibodies described herein, either alone, or with a carrier compound. Preferably, the carrier is a pharmaceutically acceptable excipient.

Other embodiments provide for use of the methods described herein in combination with one or more other treatment regimens. For example, one or more peptides of the current invention and/or one or more antibodies specific for peptides of the current invention may be used in combination with or one or more peptides or antibodies targeted to inhibiting the membrane fusion step mediated by hepatitis C virus envelope protein 1. Such peptides are described in international application PCT/US2003/035666 which is herein incorporated by reference in its entirety. The HCV E2 and E1 peptides and/or antibodies may work synergistically (i.e. they may be active at lower concentrations in combination that when used separately) or they may act in a complimentary or additive fashion.

It is noted that any combination of the modifications listed above is considered as part of the instant invention.

EXAMPLES

Example 1

Identification of Hepatitis Virus E2 Peptides that Inhibit Infectivity Mediated by HCV Envelope Proteins The selective association of a virus with a target cell is usually determined by an interaction between the viral surface glycoproteins and specific receptor or receptors on the cell surface. Receptor-binding is an essential step in the initiation of infection, and precedes other steps such as fusion between the virus and cellular membranes. Virion: receptor interaction(s) can define the host range and cellular or tissue tropism of a virus and may determine pathogenicity. HCV encodes two putative surface glycoproteins, E1 and E2, which are both believed to have carboxyl terminal transmembrane domains that anchor them in the virion envelope. In vitro expression studies have shown that E1 and E2 associate to form heterodimers, which accumulate in the endoplasmic reticulum (ER), the proposed site for HCV assembly and budding (Flint et al., 2004). Several lines of evidence indicate that E2 is the receptor binding protein (Flint and McKeating, 2000). It has been suggested that E1 is the HCV fusion protein (Flint et al., 1999; Garry and Dash, 2003). Other studies, however, indicate that E2, has a class II viral fusion protein structure and represented the fusion protein of HCV (Yagnik et al., 2000), and it is possible that both HCV E1 and E2 have a role in membrane fusion. The lack of in vitro systems for HCV propagation has hampered biological and physiochemical studies on the virion and its mechanism(s) of cell entry, and the cellular receptors remain unknown. HCV purified from plasma has been reported to exist in association with plasma lipoproteins, suggesting that the virus may use the low-density lipoprotein receptor (LDLR) to gain entry into cells (Agnello et al., 1999. Truncated soluble versions of E2 have been reported to bind specifically to human cells and were used to identify interactions with CD81 (Pileri et al., 1998; Roccasecca et al., 2003; Cormier et al., 2004), scavenger receptor class B type 1 (SR-B1) (Scarselli et al., 2002), and dendritic cell-specific intercellular adhesion molecule 3 grabbing nonintegrin (DC-SIGN) (Pohlmann et al., 2003). The results suggest that E2 may represent a target to develop peptide drugs against hepatitis C virus infection.

Materials And Methods

To overcome the lack of a conventional cell culture system for the propagation of HCV, infectious pseudotype viruses expressing HCV envelope glycoproteins have been generated (Hsu et al., 2003). Pseudotypes with HIV core proteins and HCV envelope proteins were generated by cotransfection of 293-T cells with equal amounts of plasmids expressing HCV E1 and E2 of strain H77 and the HIV envelope-defective proviral genome, pNL4.3.Luc.R$^-$E$^-$ (Pohlmann et al., 2003). Peptides from an 18 mer peptide set, overlapping by 7-10 amino acids and representing the entire amino acid sequence of E2 of HCV strain H77 (genotype 1a) and the entire amino acid sequence of HCV strain J4 (genotype 1b) were solubilized in 20% DMSO and diluted (final DMSO concentration <2%). Peptides were incubated at 37° C. with p24 antigen-normalized HCV pseudotype viral supernatants. The average concentration of peptides was ~25 µM, however, actual concentrations of some peptides in solution were 10 µM or less due to low solubility in DMSO. Supernatants were also treated with DMSO vehicle alone or with a Mab (monoclonal antibody) to HCV E2 known to neutralize pseudotype infectivity. Peptide treated and control HCV pseudotypes were added to cells, incubated for 16 hrs, virus removed and cells incubated at 37° C. for 72 h. Cell lysates were then tested for luciferase activity as described (Hsu et al., 2003).

Results and Discussion

Fifty HCV H77 1a E2 peptides were tested in the HCV infectivity assay, and nine demonstrated greater than 70% inhibition of infectivity, with several demonstrating approximately 95% inhibition (Table 7). Of 46 HCV J4 1b E2 peptides tested four demonstrated greater than 70% inhibition of infectivity (Table 8). Several of the inhibitory peptides were overlapping in the E2 sequence, for example HCV H77 1a E2 peptides 4 and 5, 32 and 33, and 43, 44, 45 and 46 (FIG. 1). This result suggests that any of several peptides targets to a particular region may be inhibitory. A comparison of the two sets of E2 peptides, H77 and J4, reveals that while similar peptides can be inhibitory (i.e., peptides 32, 33 and 108, 109), while other peptides with closely related sequences are not inhibitory (i.e., peptides 4, 5, and 99).

Selected E2 inhibitory peptides were added to pseudotypes containing the core proteins of HIV and murine leukemia, virus surface, and transmembrane glycoproteins (MuLV SU and TM), or vesicular stomatitis virus glycoprotein (VSV G). These peptides inhibited pseudotypes with HCV E1 and E2 (FIG. 2A), but failed to significantly inhibit the MuLV or VSV pseudotypes (FIGS. 2B and 2C). The results indicate that these HCV E2 inhibitory peptides are specific for inhibition of the infectivity of HCV. These results also demonstrate the potential of E2 peptides as antiHCV drugs.

TABLE 7

Identification of HCV E2 inhibitory peptides (strain H77) that inhibit HCV infectivity.

| HCV H77 1a peptide # | Luciferase units† | Percent inhibition |
|---|---|---|
| 1 | 250,376 | 44.1 |
| 2 | 447,336 | 0.2 |
| 3 | 447,906 | 0.05 |
| 4 | 10,620 | 97.6 |
| 5 | 48,000 | 89.3 |
| 6 | 503,446 | −12.3 |
| 7 | 381,340 | 14.9 |
| 8 | 113,650 | 74.6 |
| 9 | 501,126 | −11.8 |
| 10 | 334,196 | 25.4 |
| 11 | 360,410 | 19.6 |
| 12 | 417,706 | 6.8 |
| 13 | 313,323 | 31.1 |
| 14 | 279,626 | 37.6 |
| 15 | 253,410 | 43.5 |
| 16 | 403,430 | 10.0 |
| 17 | 254,516 | 43.2 |
| 18 | 435,026 | 2.9 |
| 19 | 301,406 | 32.7 |
| 20 | 231,373 | 48.4 |
| 21 | 242,223 | 45.9 |
| 22 | 245,900 | 45.2 |
| 23 | 367,916 | 17.9 |
| 24 | 391,886 | 19.7 |
| 25 | 480,280 | 7.2 |
| 26 | 216,706 | 51.6 |
| 27 | 575,206 | −28.4 |
| 28 | 394,780 | 11.9 |
| 29 | 297,353 | 33.6 |
| 30 | 655,040 | −46.2 |
| 31 | 419,263 | 6.4 |
| 32 | 85,086 | 81.0 |
| 33 | 22,406 | 95.0 |
| 34 | 354,696 | 21.8 |
| 35 | 153,553 | 66.7 |
| 36 | 535,016 | −19.5 |
| 37 | 585,553 | −30.7 |
| 38 | 345,110 | 23.0 |
| 39 | 400,756 | 11.6 |
| 40 | 442,346 | 1.3 |
| 41 | 434,743 | 3.0 |
| 42 | 353,516 | 19.1 |
| 43 | 32,283 | 92.8 |
| 44 | 91,266 | 79.6 |
| 45 | 24,703 | 94.5 |
| 46 | 103,040 | 77.0 |
| 47 | 195,320 | 56.4 |
| 48 | 290,786 | 35.1 |
| 49 | 307,310 | 31.4 |

TABLE 7-continued

Identification of HCV E2 inhibitory peptides (strain H77) that inhibit HCV infectivity.

| HCV H77 1a peptide # | Luciferase units† | Percent inhibition |
|---|---|---|
| 50 | 58,790 | 87.9 |
| VIRUS ALONE | 448,123 | |
| Virus plus anti-E2 2/69a | 10,309 | 97.6 |
| Virus plus anti-E2 9/27 | 3,567 | 99.2 |

†The numbers represent the number of luciferase units (lumens) produced after infection by either the HCV or the MLV pseudotype in the presence of the peptide at a concentration of ~25 µM. Results above 70% inhibition are indicated in bold-face type.

TABLE 8

Identification of HCV E2 inhibitory peptides (strain J4) that inhibit HCV infectivity.

| HCV J4 1b peptide # | Luciferase units† | Percent inhibition |
|---|---|---|
| 54 | 372,393 | 17.9 |
| 81 | 480,623 | −7.3 |
| 82 | 173,156 | 61.4 |
| 83 | 518,993 | −15.8 |
| 84 | 392,023 | 12.5 |
| 85 | 112,260 | 74.9 |
| 51 | 237,086 | 47.1 |
| 86 | 398,110 | 11.2 |
| 87 | 399,700 | 10.8 |
| 88 | 412,776 | 7.9 |
| 89 | 449,293 | −0.3 |
| 90 | 423,326 | 5.5 |
| 91 | 160,883 | 69.1 |
| 92 | 372,400 | 16.9 |
| 93 | 409,220 | 9.7 |
| 94 | 311,736 | 30.4 |
| 95 | 538,110 | −20.1 |
| 96 | 544,596 | −21.5 |
| 97 | 218,673 | 51.2 |
| 98 | 467,636 | −4.4 |
| 99 | 111,043 | 75.2 |
| 100 | 518,190 | −15.6 |
| 101 | 502,096 | −12.0 |
| 102 | 377,216 | 15.8 |
| 103 | 305,690 | 31.8 |
| 104 | 419,876 | 6.3 |
| 105 | 552,170 | −23.2 |
| 106 | 193,533 | 60.4 |
| 107 | 402,976 | 11.1 |
| 108 | 40,853 | 90.9 |
| 109 | 96,893 | 79.4 |
| 110 | 602,506 | −34.5 |
| 111 | 632,613 | −39.2 |
| 112 | 527,950 | −17.8 |
| 113 | 570,553 | −27.3 |
| 114 | 270,190 | 39.7 |
| 115 | 475,713 | −6.2 |
| 116 | 394,096 | 12.1 |
| 117 | 359,236 | 19.8 |
| 119 | 69,220 | 84.6 |
| 120 | 463,243 | −3.4 |
| 121 | 338,200 | 24.5 |

†The numbers represent the number of luciferase units (lumens) produced after infection by either the HCV or the MLV pseudotype in the presence of the peptide at a concentration of ~25 µM. Samples were compared to controls described in Table 7. Results above 70% inhibition are indicated in bold-face type.

TABLE 9

Sequence and location of peptides shown in Table 7.

HCV 1a H77

| peptide # | Peptide location* | Amino acid Sequence | HCV E2 IP overlap |
|---|---|---|---|
| 1 | 379-396 | AGVDAETHVTGGSAGRTT (SEQ ID NO 43) | |
| 2 | 386-403 | HVTGGSAGRTTAGLVGLL (SEQ ID NO 44) | |
| 3 | 393-410 | GRTTAGLVGLLTPGAKQN (SEQ ID NO 45) | HCV E2IP 1 |
| 4 | 399-417 | VGLLTPGAKQNIQLINTN (SEQ ID NO 46) | HCV E2IP 1 |
| 5 | 407-424 | AKQNIQLINTNGSWHINS (SEQ ID NO 47) | HCV E2IP 1 |
| 6 | 414-431 | INTNGSWHINSTALNCNE (SEQ ID NO 48) | HCV E2IP 1 |
| 7 | 421-438 | HINSTALNCNESLNTGWL (SEQ ID NO 49) | HCV E2IP 1/2 |
| 8 | 428-445 | NCNESLNTGWLAGLFYQH (SEQ ID NO 50) | HCV E2IP 2 |
| 9 | 442-459 | FYQHKFNSSGCPERLASC (SEQ ID NO 51) | HCV E2IP 2 |
| 10 | 449-466 | SSGCPERLASCRRLTDFA (SEQ ID NO 52) | |
| 11 | 456-473 | LASCRRLTDFAQGWGPIS (SEQ ID NO 53) | |
| 12 | 463-480 | TDFAQGWGPISYANGSGL (SEQ ID NO 54) | |
| 13 | 470-487 | GPISYANGSGLDERPYCW (SEQ ID NO 55) | |
| 14 | 477-494 | GSGLDERPYCWHYPPRPC (SEQ ID NO 56) | |
| 15 | 486-501 | PYCWHYPPRPCGIVPAKS (SEQ ID NO 57) | |
| 16 | 491-508 | PRPCGIVPAKSVCGPVYC (SEQ ID NO 58) | |
| 17 | 501-515 | PAKSVCGPVYCFTPSPVV (SEQ ID NO 59) | |
| 18 | 505-522 | PVYCFTPSPVVVGTTDRS (SEQ ID NO 60) | |
| 19 | 512-529 | SPVVVGTTDRSGAPTYSW (SEQ ID NO 61) | HCV E2IP 3 |
| 20 | 526-543 | TYSWGANDTDVFVLNNTR (SEQ ID NO 62) | HCV E2IP 3 |
| 21 | 533-550 | DTDVFVLNNTRPPLGNWF (SEQ ID NO 63) | HCV E2IP 3 |
| 22 | 540-557 | NNTRPPLGNWFGCTWMNS (SEQ ID NO 64) | HCV E2IP 3 |
| 23 | 547-564 | GNWFGCTWMNSTGFTKVC (SEQ ID NO 65) | HCV E2IP 3 |
| 24 | 554-571 | WMNSTGFTKVCGAPPCVI (SEQ ID NO 66) | HCV E2IP 3 |
| 25 | 561-578 | TKVCGAPPCVIGGVGNNT (SEQ ID NO 67) | |
| 26 | 568-585 | PCVIGGVGNNTLLCPTDC (SEQ ID NO 68) | |
| 27 | 575-592 | GNNTLLCPTDCFRKHPEA (SEQ ID NO 69) | |
| 28 | 582-599 | PTDCFRKHPEATYSRCGS (SEQ ID NO 70) | |
| 29 | 589-606 | HPEATYSRCGSGPWITPR (SEQ ID NO 71) | |
| 30 | 596-613 | RCGSGPWITPRCMVDYPY (SEQ ID NO 72) | HCV E2IP 4 |
| 31 | 603-620 | ITPRCMVDYPYRLWHYPC (SEQ ID NO 73) | HCV E2IP 4 |
| 32 | 610-627 | DYPYRLWHYPCTINYTIF (SEQ ID NO 74) | HCV E2IP 4 |
| 33 | 617-634 | HYPCTINYTIFKVRMYVG (SEQ ID NO 75) | HCV E2IP 4 |
| 34 | 624-641 | YTIFKVRMYVGGVEHRLE (SEQ ID NO 76) | HCV E2IP 4 |
| 35 | 631-648 | MYVGGVEHRLEAACNWTR (SEQ ID NO 77) | HCV E2IP 4 |
| 36 | 638-655 | HRLEAACNWTRGERCDLE (SEQ ID NO 78) | |
| 37 | 645-662 | NWTRGERCDLEDRDRSEL (SEQ ID NO 79) | |
| 38 | 652-669 | CDLEDRDRSELSPLLLST (SEQ ID NO 80) | |
| 39 | 659-676 | RSELSPLLLSTTQWQVLP (SEQ ID NO 81) | |
| 40 | 666-683 | LLSTTQWQVLPCSFTTLP (SEQ ID NO 82) | |
| 41 | 673-690 | QVLPCSFTTLPALSTGLI (SEQ ID NO 83) | HCV E2IP 5 |
| 42 | 680-697 | TTLPALSTGLIHLHQNIV (SEQ ID NO 84) | HCV E2IP 5 |
| 43 | 687-704 | TGLIHLHQNIVDVQYLYG (SEQ ID NO 85) | HCV E2IP 5 |
| 44 | 694-711 | QNIVDVQYLYGVGSSIAS (SEQ ID NO 86) | HCV E2IP 5 |
| 45 | 701-718 | YLYGVGSSIASWAIKWEY (SEQ ID NO 87) | HCV E2IP 5 |
| 46 | 708-725 | SIASWAIKWEYVVLLFLL (SEQ ID NO 88) | HCV E2IP 5/6 |
| 47 | 715-732 | KWEYVVLLFLLLADARVC (SEQ ID NO 89) | HCV E2IP 5/6 |
| 48 | 722-739 | LFLLLADARVCSCLWMML (SEQ ID NO 90) | HCV E2IP 6 |
| 49 | 729-746 | ARVCSCLWMMLLISQAEA (SEQ ID NO 91) | HCV E2IP 6 |
| 50 | 756-773 | WMMLLISQAEAALENLVI (SEQ ID NO 92) | HCV E2IP 6 |

*Numbering refers to the numbering provided at Genbank Accession NP_671491

TABLE 10

Sequence and location of peptides shown in Table 8.

HCV 1b J4

| peptide # | Peptide location* | Amino acid sequence | HCV E2 IP overlap |
|---|---|---|---|
| 54 | (379-396) | AGVDGETHTTGRVAGHTT (SEQ ID NO 93) | |
| 80 | (386-403) | HTTGRVAGHTTSGFTSLF (SEQ ID NO 94) | HCV E2IP 1 |
| 81 | (393-410) | GHTTSGFTSLFSSGASQK (SEQ ID NO 95) | HCV E2IP 1 |
| 82 | (400-417) | TSLFSSGASQKIQLVNTN (SEQ ID NO 96) | HCV E2IP 1 |
| 83 | (407-424) | ASQKIQLVNTNGSWHINR (SEQ ID NO 97) | HCV E2IP 1 |
| 84 | (421-438) | HINRTALNCNDSLQTGFF (SEQ ID NO 98) | HCV E2IP 1/2 |
| 85 | (428-445) | NCNDSLQTGFFAALFYAH (SEQ ID NO 99) | HCV E2IP 2 |

TABLE 10-continued

Sequence and location of peptides shown in Table 8.

| HCV 1b J4 peptide # | Peptide location* | Amino acid sequence | HCV E2 IP overlap |
|---|---|---|---|
| 51 | (435-452) | TGFFAALFYAHKFNSSGC (SEQ ID NO 100) | HCV E2IP 2 |
| 86 | (442-459) | FYAHKFNSSGCPERMASC (SEQ ID NO 101) | HCV E2IP 2 |
| 87 | (449-466) | SSGCPERMASCRPIDWFA (SEQ ID NO 102) | |
| 88 | (456-473) | MASCRPIDWFAQGWGPIT (SEQ ID NO 103) | |
| 89 | (463-480) | DWFAQGWGPITYTKPNSS (SEQ ID NO 104) | |
| 90 | (477-494) | PNSSDQRPYCWHYAPRPC (SEQ ID NO 105) | |
| 91 | (484-501) | PYCWHYAPRPCGVVPASQ (SEQ ID NO 106) | |
| 92 | (491-508) | PRPCGVVPASQVCGPVYC (SEQ ID NO 107) | |
| 93 | (498-515) | PASQVCGPVYCFTPSPVV (SEQ ID NO 108) | |
| 94 | (505-522) | PVYCFTPSPVVVGTTDRS (SEQ ID NO 109) | |
| 95 | (512-529) | SPVVVGTTDRSGVPTYSW (SEQ ID NO 110) | HCV E2IP 3 |
| 96 | (519-536) | TDRSGVPTYSWGENETDV (SEQ ID NO 111) | HCV E2IP 3 |
| 97 | (526-543) | TYSWGENETDVMLLNNTR (SEQ ID NO 112) | HCV E2IP 3 |
| 98 | (533-550) | ETDVMLLNNTRPPQGNWF (SEQ ID NO 113) | HCV E2IP 3 |
| 99 | (540-557) | NNTRPPQGNWFGCTWMNS (SEQ ID NO 114) | HCV E2IP 3 |
| 100 | (554-571) | WMNSTGFTKTCGGPPCNI (SEQ ID NO 115) | HCV E2IP 3 |
| 101 | (561-578) | TKTCGGPPCNIGGVGNRT (SEQ ID NO 116) | |
| 102 | (568-585) | PCNIGGVGNRTLICPTDC (SEQ ID NO 117) | |
| 103 | (575-592) | GNRILICPTDCFRKHPEA (SEQ ID NO 118) | |
| 104 | (582-599) | PTDCFRKHPEATYTKCGS (SEQ ID NO 119) | |
| 105 | (589-606) | HPEATYTKCGSGPWLTPR (SEQ ID NO 120) | |
| 106 | (596-613) | KCGSGPWLTPRCLVDYPY (SEQ ID NO 121) | HCV E2IP 4 |
| 107 | (603-620) | LTPRCLVDYPYRLWHYPC (SEQ ID NO 122) | HCV E2IP 4 |
| 108 | (610-627) | DYPYRLWHYPCTLNFSIF (SEQ ID NO 123) | HCV E2IP 4 |
| 109 | (617-634) | HYPCTLNFSIFKVRMYVG (SEQ ID NO 124) | HCV E2IP 4 |
| 110 | (631-648) | MYVGGVEHRLNAACNWTR (SEQ ID NO 125) | HCV E2IP 4 |
| 111 | (638-655) | HRLNAACNWTRGERCNLE (SEQ ID NO 126) | |
| 112 | (645-662) | NWTRGERCNLEDRDRSEL (SEQ ID NO 127) | |
| 113 | (652-669) | CNLEDRDRSELSPLLLST (SEQ ID NO 128) | |
| 114 | (659-676) | RSELSPLLLSTTEWQILP (SEQ ID NO 129) | |
| 115 | (666-683) | LLSTTEWQILPCAFTTLP (SEQ ID NO 130) | |
| 116 | (673-690) | QILPCAFTTLPALSTGLI (SEQ ID NO 131) | HCV E2IP 5 |
| 117 | (680-697) | TTLPALSTGLIHLHQNIV (SEQ ID NO 132) | HCV E2IP 5 |
| 118 | (694-711) | QNIVDVQYLYGVGSAFVS (SEQ ID NO 133) | HCV E2IP 5 |
| 119 | (708-725) | AFVSFAIKWEYILLLFLL (SEQ ID NO 134) | HCV E2IP 5/6 |
| 120 | (722-739) | LFLLLADARVCACLWMML (SEQ ID NO 135) | HCV E2IP 6 |
| 121 | (729-746) | ARVCACLWMMLLIAQAEA (SEQ ID NO 136) | HCV E2IP 6 |

*Numbering refers to the numbering provided at Genbank Accession BAA01583

The peptides of Tables 7-10 are an overlapping set of peptides representing E2 of two strains of HCV (H77 and J4). SEQ ID NO's 1-6 are longer versions of the "hits" highlighted in yellow in Tables 7-10. The rationale for the design of SEQ ID NOs:1-6 is that the optimum inhibitory peptide may be include flanking sequences), and that the ultimate optimum peptide may be a fragment of this longer peptide. SEQ ID NOs:7-42 are variants of SEQ ID NOs:1-6 representing analogous sequences from the E2 proteins of the other major genotypes of HCV.

Example 2

Proteomic Computational Model of HCV E2

Because HCV cannot be propagated in cell culture, insufficient numbers of virions are available to perform structural analyses. Thus, the molecular structure of HCV E2 has not been determined and is currently unknown. In the absence of an X-ray crystallographic structure of HCV E2, it is possible to derive useful structural information using newly developed computational analyses supplemented by comparisons to other viral glycoproteins of known structure. Such a model of HCV E2 can be useful in defining the potential mechanisms of action of E2 inhibitory peptides.

Materials and Methods

Representatives of the most common subtypes of hepatitis C virus were used for sequence and structural comparisons. The strains examined a human prototype HCV strain H77 (subtype 1a, Genbank Accession NP_751921), strain HC-J4 (subtype 1b, Genbank Accession BAA01583), strain NDM59 (subtype 2a, Genbank Accession AF169005), strain TrKj (subtypes 3b, Genbank Accession D49374), strain ED43 (subtype 4a, Genbank Accession Y11604), strain EUH1480 (subtype 5a , Genbank Accession Y13184), strain euhk2 (subtype 6a, Genbank Accession Y12083).

Methods to derive general models of surface glycoproteins have been described previously (Gallaher et al., 1989). PRSS3, a program derived from rdf2 (Pearson and Lipman, 1988), which uses the Smith-Waterman sequence alignment algorithm (Smith and Waterman, 1981), was used to determine the significance of protein alignments. PRSS3 is part of the FASTA package of sequence analysis programs available by anonymous ftp from ftp.virginia.edu. Default settings for PRSS3 were used, including the blosum50 scoring matrix, gap opening penalty of 12, and gap extension penalty of 2. MacMolly (Soft Gene GmbH, Berlin) was used to locate areas of limited sequence similarity and to perform Chou-Fasman and Robson-Gamier analyses (Biou et al., 1988; Chou and Fasman, 1974). PHDsec (Columbia University Bioinformatics Center, http://cubic.bioc.columbia.edu/predictprotein/) was the preferred method of secondary structure prediction (Rost and Liu, 2003). PHDsec predicts secondary structure from multiple sequence alignments by a system of neural networks, and is rated at an expected average accuracy of 72% for three states, helix, strand and loop. Domains with significant propensity to form transmembrane helices were identified with TMpred (ExPASy, Swiss Institute of Bioinformatics, http://www.ch.embnet.org/software/TMPRED_form.html). TMpred is based on a statistical analysis of TMbase, a database of naturally occurring transmembrane glycoproteins (Hofmann and Stoffel, 1993). Sequences with a propensity to partition into the lipid bilayer were identified with Membrane Protein eXplorer version 2.2a from the Stephen White laboratory using default settings (White et al., 2003).

Results and Discussion

Figure 3:
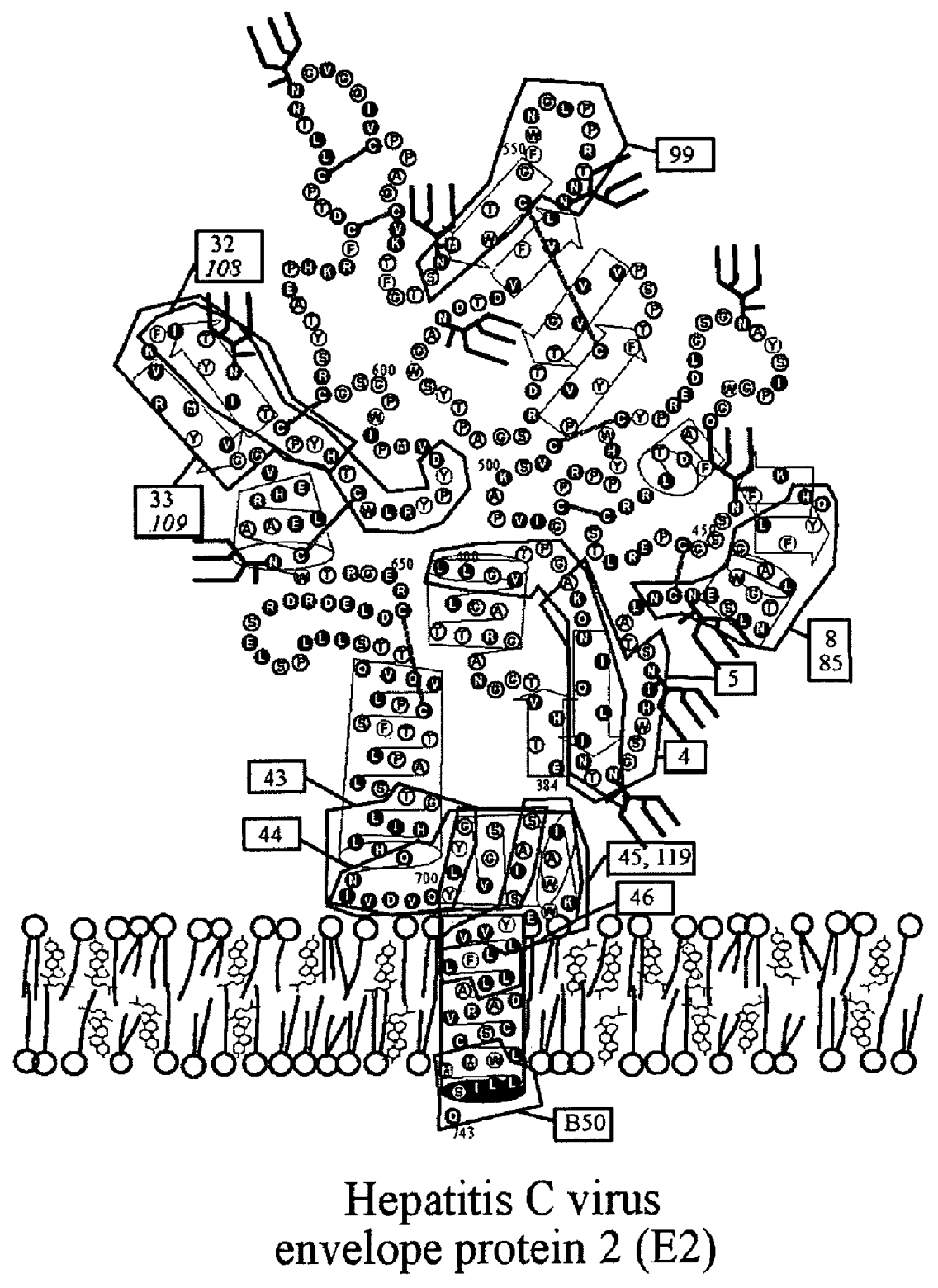

A two-dimensional model of HCV E2 was developed based on the application of proteomics computational analyses and comparison to the known structures of other receptor-binding viral envelope proteins (FIG. 3). The HCV E2 secondary structure structures drawn in FIG. 3 conform to the PHDsec secondary structure alignment algorithm and are also generally consistent with both Chou-Fasman and Robson-Garnier predictions. An important feature of the E2 model is the predominance of beta sheet structures in the amino terminal two-thirds of the molecule and alpha helical structures in the carboxyl terminal third of the molecule. Dicysteine linkages were predicted on the basis of comparison to the envelope glycoproteins of retroviruses. In retroviral envelope proteins adjacent cysteines that are separated by greater than 15 amino acids are typically covalently bonded to each other. Clusters of four cysteines that are each separated by fewer than 15 amino acids are typically covalently bonded to a nonadjacent cysteine in the cluster. The first two long predicted alpha helices in the carboxyl terminal third of E2 form a predicted stem structure analogous to the stem region of other flavivirus envelope proteins (Allison et al., 1999). The depicted transmembrane domain structure was predicted by the TMPRED algorithm.

Figure 4:
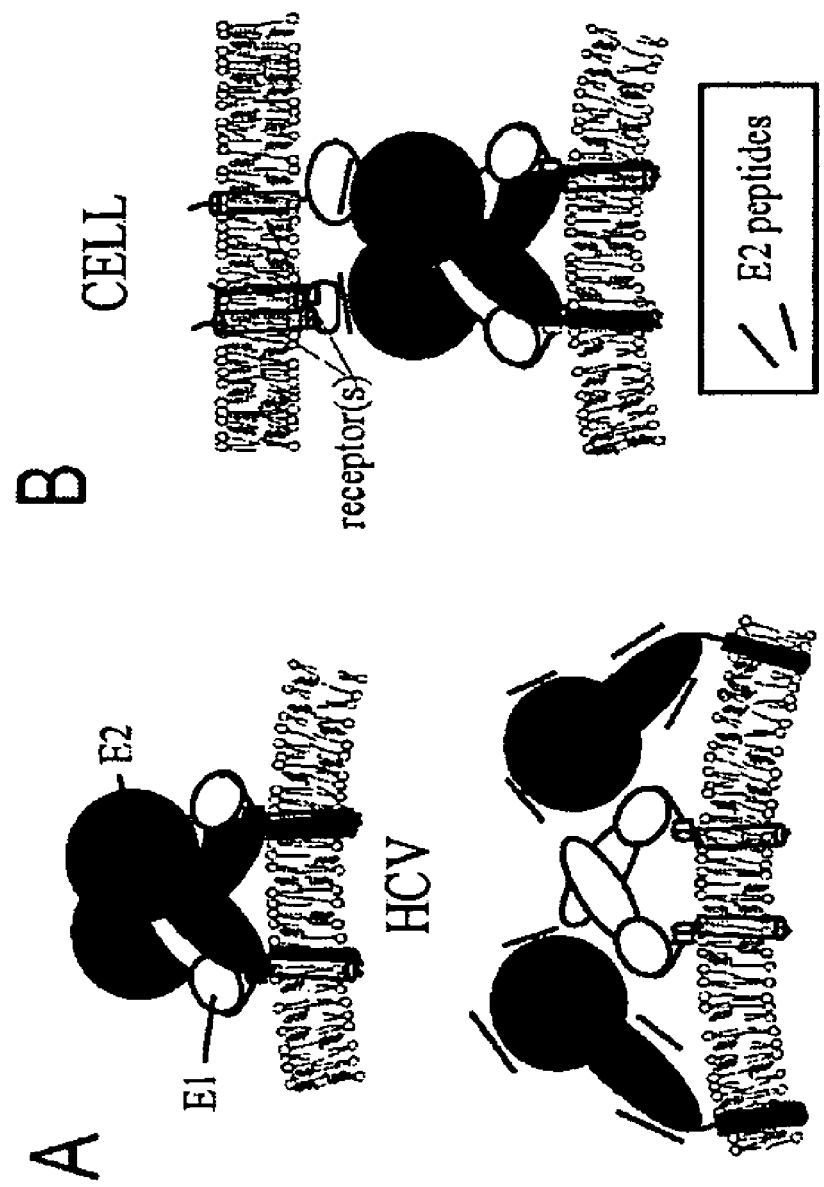
FIG. 4. Model depicting pre-fusion site of action of HCV E2 peptides. Panel A. HCV E2 peptides disruption of E1-E2 interactions or E2-E2 interactions in HCV virions. Panel B: HCV E2 disruption of HCV virion-receptor interactions.

HCV E2 inhibitory peptides map to regions on the HCV E2 model that correspond to an amino terminal region, a cysteine cluster, the stem and transmembrane domain (shaded regions in FIG. 3). These domains of HCV E2 can be involved in hepatitis C virus receptor binding, E2 structural rearrangements or protein-protein interactions, or other pre-fusion steps. HCV E2 inhibitory peptides can be used to interfere with these early steps in HCV infection as depicted in FIG. 4.

The present invention is not to be to be construed as limited in scope by the specific embodiments described herein. Rather, the specific embodiments described are only illustrative. Indeed, various modifications of the invention in addition to those described herein will become apparent to those skilled in the art from the foregoing description and accompanying figures. Such modifications are intended to fall within the scope of the claims. Various publications are cited herein, the disclosures of each of which is incorporated by reference in its entirety. Citation or identification of any reference in any section of this application shall not be construed as an admission that such reference is available as prior art to the present invention

REFERENCES

Each of the following is herein incorporated by reference in its entirety.

Agnello, V., G. Abel, M. Elfahal, G. B. Knight, and Q. X. Zhang. (1999). Hepatitis C virus and other flaviviridae viruses enter cells via low density lipoprotein receptor. *Proc. Natl. Acad. Sci. USA* 96,12766-12771.

Allison, S. L., Schalich, J., Stiasny, K., Mandl, C. W., and Heinz, F. X. (2001). Mutational evidence for an internal fusion peptide in flavivirus envelope protein E. *J. Virol.* 75, 4268-75.

Allison, S. L., Stiasny, K., Stadler, K., Mandl, C. W., and Heinz, F. X. (1999). Mapping of functional elements in the stem-anchor region of tick-borne encephalitis virus envelope protein E. *J. Virol.* 73, 5605-12.

Barth, H., Schafer, C., Adah, M. I., Zhang, F., Linhardt, R. J., Toyoda, H., Kinoshita-Toyoda, A., Toida, T., Van Kuppevelt, T. H., Depla, E., Von Weizsacker, F., Blum, H. E., and Baumert, T F. (2003). Cellular binding of hepatitis C virus envelope glycoprotein E2 requires cell surface heparan sulfate. *J. Biol. Chem.* 278, 41003-12.

Bartosch, B., Vitelli, A., Granier, C., Goujon, C., Dubuisson, J., Pascale, S., Scarselli, E., Cortese, R., Nicosia, A., and Cosset, F. L. (2003). Cell entry of hepatitis C virus requires a set of co-receptors that include the CD81 tetraspanin and the SR-B1 scavenger receptor. *J. Biol. Chem.* 278, 41624-30.

Biou, V., Gibrat, J. F., Levin, J. M., Robson, B., and Garnier, J. (1988). Secondary structure prediction: combination of three different methods. *Protein Engineering* 2, 185-91.

Bressanelli, S., Stiasny, K., Allison, S. L., Stura, E. A., Duquerroy, S., Lescar, J., Heinz, F. X., and Rey, F. A. (2004). Structure of a flavivirus envelope glycoprotein in its low-pH-induced membrane fusion conformation. *EMBO J.* 23, 728-38.

Chou, P. Y., and Fasman, G. D. (1974). Prediction of protein conformation. Biochemistry 13, 222-45.

Clark-Lewis, I., Aebersold, R., Ziltener, H., Schrader, J. W., Hood, L. E., and Kent, S. B. (1986). Automated chemical synthesis of a protein growth factor for hemopoietic cells, interleukin-3. *Science* 231, 134-9.

Colombo, M. (2000). Hepatocellular carcinoma in patients with HCV. *Baillieres Best Pract. Res. Clin. Gastroenterol.* 14, 327-39.

Cormier, E. G., Tsamis, F., Kajumo, F., Durso, R. J., Gardner, J. P., and Dragic, T. (2004). CD81 is an entry coreceptor for hepatitis C virus. Proc. Natl. Acad. Sci. USA. 101, 7270-4.

Flint, M., Thomas, J. M., Maidens, C. M., Shotton, C., Levy, S., Barclay, W. S., and McKeating, J. A. (1999). Functional analysis of cell surface-expressed hepatitis C virus E2 glycoprotein. *J. Virol.* 73, 6782-90.

Flint, M., and McKeating, J. A. (2000). The role of the hepatitis C virus glycoproteins in infection. Rev. Med Virol. 10, 101 - 17.

Flint, M., Logvinoff, C., Rice, C. M., and McKeating, J. A. (2004). Characterization of infectious retroviral pseudotype particles bearing hepatitis C virus glycoproteins. *J. Virol.* 78, 6875-82.

Gallaher, W. R. (1987). Detection of a fusion peptide sequence in the transmembrane protein of human immunodeficiency virus. *Cell* 50, 327-8.

Gallaher, W. R. (1996). Similar structural models of the transmembrane glycoproteins of Ebola and avian sarcoma viruses. *Cell* 85, 1-2.

Gallaher, W. R., BALL, J. M., GARRY, R. F., GRIFFIN, M. C., and MONTELARO, R. C. (1989). A general model for the transmembrane proteins of HIV and other retroviruses. *AIDS Res. Hum. Retro.* 5, 431-40.

Gallaher, W. R., DiSIMONE, C., and BUCHMEIER, M. J. (2001). The viral transmembrane superfamily: possible divergence of Arenavirus and Filovirus glycoproteins from a common RNA virus ancestor. *BMC Microbiol.* 1, 1.

Garry, R. F. and DASH S. (2003). Proteomics computational analysis suggest that hepatitis C virus E1 and pestivirus E2 envelope glycoproteins are truncated class II fusion proteins. *Virology* 307, 255-65.

Gibbons, D. L., Vaney, M. C., Roussel, A., Vigouroux, A., Reilly, B., Lepault, J., Kielian, M., and Rey, F. A. (2004). Conformational change and protein-protein interactions of the fusion protein of Semliki Forest virus. *Nature* 427, 320-5.

Hofmann, K., and Stoffel, W. (1993). TMbase—a database of membrane-spanning segments. *Biol. Chem. Hoppe-Seyler* 374, 166.

Hsu, M., Zhang, J., Flint, M., Logvinoff, C., Cheng-Mayer, C., Rice, C. M., and mckeating, j. a. (2003). Hepatitis C virus glycoproteins mediate pH-dependent cell entry of pseudotyped retroviral particles. *Proc. Natl. Acad. Sci. USA* 100, 7271-6.

Jardetzky, T. S., and Lamb, R. A. (2004). Virology: a class act. Nature 427(6972), 307-8.

Kuhn, R. J., ZHANG, W., ROSSMANN, M. G., PLETNEV, S. V., CORVER, J., LENCHES, E., JONES, C. T., MUKHOPADHYAY, S., CHIPMAN, P. R., STRAUSS, E. G., BAKER, T. S., and STRAUSS, J. H. (2002). Structure of dengue virus: implications for flavivirus organization, maturation, and fusion. *Cell* 108, 717-25.

Kwong, P. D., R. Wyatt, J. Robinson, R. W. Sweet, J. Sodroski, and W. A. Hendrickson. 1998. Structure of an HIV gp120 envelope glycoprotein in complex with the CD4 receptor and a neutralizing human antibody. *Nature* 393, 648-59.

Lalezari, J. P., E. DeJesus, D. W. Northfelt, G. Richmond, P. Wolfe, R. Haubrich, D. Henry, W. Powderly, S. Becker, M. Thompson, F. Valentine, D. Wright, M. Carlson, S. Riddler, F. F. Haas, R. DeMasi, P. R. Sista, M. Salgo, and J. Delehanty. 2003. A controlled Phase II trial assessing three doses of enfuvirtide (T-20) in combination with abacavir, amprenavir, ritonavir and efavirenz in non-nucleoside reverse transcriptase inhibitor-naive HIV-infected adults. *Antivir. Ther.* 8, 279-87.

Lescar, J., ROUSSEL, A., WIEN, M. W., NAVAZA, J., FULLER, S. D., WENGLER, G., and REY, F. A. (2001). The fusion glycoprotein shell of Semliki Forest virus: an icosahedral assembly primed for fusogenic activation at endosomal pH. *Cell* 105, 137-48.

McKeating, J. A. Understanding hepatitis C virus. Gut, in press.

Modis, Y., Ogata, S., Clements, D., and Harrison, S. (2004). Structure of the dengue virus envelope protein after membrane fusion. Nature 427, 313-319.

Pearson, W. R., and Lipman, D. J. (1988). Improved tools for biological sequence comparison. *Proc. Natl. Acad. Sci. USA* 85, 2444-8.

Pileri, P., Y. Uematsu, S. Compagnoli, G. Galli, F. Falugi, R. Petracca, A. J. Weiner, M. Houghton, D. Rosa, G. Grandi, and S. Abrignani. (1998). Binding of hepatitis C virus to CD81. *Science* 282, 938-941.

Pohlmann S., Zhang J., Baribaud F., Chen Z., Leslie G. J., Lin G., Granelli-Pipemo A., Doms R. W., Rice C. M., and McKeating J. A. (2003). Hepatitis C virus glycoproteins interact with DC-SIGN and DC-SIGNR. *J. Virol.* 77, 4070-80.

Poynard, T., Yuen, M. F., Ratziu, V., and Lai, C. L. (2003). Viral hepatitis C. *Lancet* 362, 2095-100.

Qureshi, N., COY, D., GARRY, R., and HENDERSON L A (1990). Characterization of a putative cellular receptor for HIV-1 transmembrane glycoprotein using synthetic peptides. *AIDS* 4, 553-558.

Rey, F. A., HEINZ, F. X., MANDL, C., KUNZ, C., and HARRISON, S. C. (1995). The envelope glycoprotein from tick-borne encephalitis virus at 2 A resolution. *Nature* 375, 291-8.

Roccasecca, R., Ansuini, H., Vitelli, A., Meola, A., Scarselli, E., Acali, S., Pezzanera, M., Ercole, B. B., McKeating, J., Yagnik, A., Lahm, A., Tramontano, A., Cortese, R., and Nicosia, A. (2003). Binding of the hepatitis C virus E2 glycoprotein to CD81 is strain specific and is modulated by a complex interplay between hypervariable regions 1 and 2. *J. Virol.* 77, 1856-67.

Scarselli, E., H. Ansuini, R. Cerino, R. M. Roccasecca, S. Acali, G. Filocamo, C. Traboni, A. Nicosia, R. Cortese, and A. Vitelli. (2002). The human scavenger receptor class B type I is a novel candidate receptor for the hepatitis C virus. *EMBO J.* 21, 5017-5025.

Rost, B., and Liu, J. (2003). The PredictProtein server. Nucleic Acids Res 31, 3300-4.Smith, T. F., and Waterman, M. S. (1981). Identification of common molecular subsequences. J. Mol. Biol. 147, 195-7.

Strauss, J. H., and Strauss, E. G. (1994). The alphaviruses: gene expression, replication, and evolution. *Microbiol Rev.* 58, 491-562.

White, S. H., Snider, C., Jaysinghe, S., and Kim, J. (2003). Membrane Protein Explorer version 2.2a. http://blanco.biomol.uci.edu/mpex/.

Wild, C., GREENWELL, T., and MATTHEWS, T. (1 993). A synthetic peptide from HIV-1 gp41 is a potent inhibitor of virus-mediated cell-cell fusion. *AIDS Res. Hum. Retro.* 9, 1051-3.

Wild, C. T., SHUGARS, D. C., GREENWELL, T. K., McDANAL, C. B., and MATTHEWS, T. J. (1994). Peptides corresponding to a predictive alpha-helical domain of human immunodeficiency virus type 1 gp41 are potent inhibitors of virus infection. *Proc. Natl. Acad. Sci. USA* 91, 9770-4.

Wilson, I. A., SKEHEL, J. J., and WILEY, D. C. (1981). Structure of the haemagglutinin membrane glycoprotein of influenza virus at 3 A resolution. *Nature* 289, 366-73.

Yagnik, A. T., LAHM, A., MEOLA, A., ROCCASECCA, R. M., ERCOLE, B. B., NICOSIA, A., and TRAMONTANO, A. (2000). A model for the hepatitis C virus envelope glycoprotein E2. *Proteins* 40, 355-66

Zhang J., Randall G., Higginbottom A., Monk P., Rice C. M., McKeating J. A. (2004). CD81 is required for hepatitis C virus glycoprotein-mediated viral infection. *J. Virol.* 78, 1448-55.

The invention claimed is:

1. A peptide consisting of a fragment of SEQ ID NO:5 that comprises the sequence of SEQ ID NO:85, SEQ ID NO:86 or SEQ ID NO:87.

2. A peptide consisting of SEQ ID NO:5.

3. The peptide of claim 1, wherein the fragment comprises SEQ ID NO:85.

4. The peptide of claim 3, wherein the fragment consists of SEQ ID NO:85.

5. The peptide of claim 1, wherein the fragment comprises SEQ ID NO:86.

6. The peptide of claim 5, wherein the fragment consists of SEQ ID NO:86.

7. The peptide of claim 1, wherein the fragment comprises SEQ ID NO:87.

8. The peptide of claim 7, wherein the fragment consists of SEQ ID NO:87.

9. A pharmaceutical composition comprising a peptide, wherein the peptide consists of SEQ ID NO:5 or a fragment of SEQ ID NO:5 comprising SEQ ID NO:85, SEQ ID NO:86 or SEQ ID NO:87, wherein the peptide optionally has:

a) in place of an N-terminal amino group hydrogen, an N-terminal moiety that is an acetyl group, a hydrophobic group, a carbobenzoxyl group, a dansyl group, a t-butyloxycarbonyl group, or a macromolecular carrier group;

b) in place of the C-terminal carboxylate group hydroxyl, a C-terminal moiety that is an amino group, a hydrophobic group, a t-butyloxycarbonyl group or a macromolecular carrier group; or c) an amino acid residue that is in the D-isomer configuration.

10. The composition of claim 9, wherein the peptide has:
a) in place of an N-terminal amino group hydrogen, an N-terminal moiety that is an acetyl group, a hydrophobic group, a carbobenzoxyl group, a dansyl group, a t-butyloxycarbonyl group, or a macromolecular carrier group; or
b) in place of the C-terminal carboxylate group hydroxyl, a C-terminal moiety that is a hydrophobic group, a t-butyloxycarbonyl group or a macromolecular carrier group.

11. The composition of claim 10, wherein either the N-terminal moiety or the C-terminal moiety of the peptide is a macromolecular carrier group selected from a lipid conjugate, polyethylene glycol, or a carbohydrate.

12. The composition of claim 9, wherein the peptide has an amino acid that is in a D-isomer configuration.

13. A method of treating or preventing hepatitis C virus (HCV) infection in a patient, comprising administering to a patient in need thereof an effective amount of a pharmaceutical composition according to any one of claims 9-12.

14. The method of claim 13, further comprising administering to the patient an antibody produced using as an immunogen a peptide, wherein the peptide immunogen consists of SEQ ID NO:5 or a fragment of SEQ ID NO:5 comprising SEQ ID NO:85, SEQ ID NO:86 or SEQ ID NO:87.

* * * * *

SEQUENCE LISTING

<160> NUMBER OF SEQ ID NOS: 138

<210> SEQ ID NO 1
<211> LENGTH: 26
<212> TYPE: PRT
<213> ORGANISM: Artificial sequence
<220> FEATURE:
<223> OTHER INFORMATION: Synthetic peptide

<400> SEQUENCE: 1

Leu Val Gly Leu Leu Thr Pro Gly Ala Lys Gln Asn Ile Gln Leu Ile
1               5                   10                  15

Asn Thr Asn Gly Ser Trp His Ile Asn Ser
            20                  25

<210> SEQ ID NO 2
<211> LENGTH: 17
<212> TYPE: PRT
<213> ORGANISM: Artificial sequence
<220> FEATURE:
<223> OTHER INFORMATION: Synthetic peptide

<400> SEQUENCE: 2

Cys Asn Glu Ser Leu Asn Thr Gly Trp Leu Ala Gly Leu Phe Tyr Gln
1               5                   10                  15

His

<210> SEQ ID NO 3
<211> LENGTH: 34
<212> TYPE: PRT
<213> ORGANISM: Artificial sequence
<220> FEATURE:
<223> OTHER INFORMATION: Synthetic peptide

<400> SEQUENCE: 3

Tyr Ser Trp Gly Ala Asn Asp Thr Asp Val Phe Val Leu Asn Asn Thr
1               5                   10                  15

Arg Pro Pro Leu Gly Asn Trp Phe Gly Cys Thr Trp Met Asn Ser Thr
            20                  25                  30

Gly Phe

<210> SEQ ID NO 4
<211> LENGTH: 27
<212> TYPE: PRT
<213> ORGANISM: Artificial sequence
<220> FEATURE:
<223> OTHER INFORMATION: Synthetic peptide

<400> SEQUENCE: 4

Asp Tyr Pro Tyr Arg Leu Trp His Tyr Pro Cys Thr Ile Asn Tyr Thr
1               5                   10                  15

Ile Phe Lys Val Arg Met Tyr Val Gly Gly Val
            20                  25

<210> SEQ ID NO 5
<211> LENGTH: 35
<212> TYPE: PRT
<213> ORGANISM: Artificial sequence
<220> FEATURE:
<223> OTHER INFORMATION: Synthetic peptide

<400> SEQUENCE: 5

```
Ala Leu Ser Thr Gly Leu Ile His Leu His Gln Asn Ile Val Asp Val
1               5                   10                  15

Gln Tyr Leu Tyr Gly Val Gly Ser Ser Ile Ala Ser Trp Ala Ile Lys
                20                  25                  30

Trp Glu Tyr
        35

<210> SEQ ID NO 6
<211> LENGTH: 28
<212> TYPE: PRT
<213> ORGANISM: Artificial sequence
<220> FEATURE:
<223> OTHER INFORMATION: Synthetic peptide

<400> SEQUENCE: 6

Val Val Leu Leu Phe Leu Leu Leu Ala Asp Ala Arg Val Cys Ser Cys
1               5                   10                  15

Leu Trp Met Met Leu Leu Ile Ser Gln Ala Glu Ala
                20                  25

<210> SEQ ID NO 7
<211> LENGTH: 26
<212> TYPE: PRT
<213> ORGANISM: Artificial sequence
<220> FEATURE:
<223> OTHER INFORMATION: Synthetic peptide

<400> SEQUENCE: 7

Phe Thr Ser Leu Phe Ser Ser Gly Ala Ser Gln Lys Ile Gln Leu Val
1               5                   10                  15

Asn Thr Asn Gly Ser Trp His Ile Asn Arg
                20                  25

<210> SEQ ID NO 8
<211> LENGTH: 26
<212> TYPE: PRT
<213> ORGANISM: Artificial sequence
<220> FEATURE:
<223> OTHER INFORMATION: Synthetic peptide

<400> SEQUENCE: 8

Leu Ala Gly Leu Phe Thr Ser Gly Ala Lys Gln Asn Ile Gln Leu Ile
1               5                   10                  15

Asn Thr Asn Gly Ser Trp His Ile Asn Arg
                20                  25

<210> SEQ ID NO 9
<211> LENGTH: 26
<212> TYPE: PRT
<213> ORGANISM: Artificial sequence
<220> FEATURE:
<223> OTHER INFORMATION: Synthetic peptide

<400> SEQUENCE: 9

Phe Thr Ser Phe Phe Thr Arg Gly Pro Ser Gln Asp Leu Gln Leu Val
1               5                   10                  15

Asn Ser Asn Gly Ser Trp His Ile Asn Ser
                20                  25

<210> SEQ ID NO 10
<211> LENGTH: 26
<212> TYPE: PRT
<213> ORGANISM: Artificial sequence
<220> FEATURE:
```

-continued

<223> OTHER INFORMATION: Synthetic peptide

<400> SEQUENCE: 10

Leu Ala Asn Leu Phe Ser Ser Gly Ser Lys Gln Asn Leu Gln Leu Ile
1               5                   10                  15

Asn Ser Asn Gly Ser Trp His Ile Asn Arg
            20                  25

<210> SEQ ID NO 11
<211> LENGTH: 26
<212> TYPE: PRT
<213> ORGANISM: Artificial sequence
<220> FEATURE:
<223> OTHER INFORMATION: Synthetic peptide

<400> SEQUENCE: 11

Leu Thr Ser Phe Phe Asn Pro Gly Pro Gln Arg Gln Leu Gln Phe Val
1               5                   10                  15

Asn Thr Asn Gly Ser Trp His Ile Asn Ser
            20                  25

<210> SEQ ID NO 12
<211> LENGTH: 26
<212> TYPE: PRT
<213> ORGANISM: Artificial sequence
<220> FEATURE:
<223> OTHER INFORMATION: Synthetic peptide

<400> SEQUENCE: 12

Phe Ala Ser Leu Leu Thr Pro Gly Ala Lys Gln Asn Ile Gln Leu Ile
1               5                   10                  15

Asn Thr Asn Gly Ser Trp His Ile Asn Arg
            20                  25

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Cys Asn Asp Ser Leu His Thr Gly Phe Leu Ala Ala Leu Phe Tyr Thr
1               5                   10                  15

His

<210> SEQ ID NO 14
<211> LENGTH: 17
<212> TYPE: PRT
<213> ORGANISM: Artificial sequence
<220> FEATURE:
<223> OTHER INFORMATION: Synthetic peptide

<400> SEQUENCE: 14

Cys Asn Asp Ser Leu Asn Thr Gly Phe Ile Ala Ser Leu Phe Tyr Thr
1               5                   10                  15

Tyr

<210> SEQ ID NO 15
<211> LENGTH: 17
<212> TYPE: PRT
<213> ORGANISM: Artificial sequence
<220> FEATURE:
<223> OTHER INFORMATION: Synthetic peptide

<400> SEQUENCE: 15

Cys Asn Asp Ser Leu Asn Thr Gly Phe Ile Ala Gly Leu Phe Tyr Tyr
1               5                   10                  15

His

<210> SEQ ID NO 16
<211> LENGTH: 17
<212> TYPE: PRT
<213> ORGANISM: Artificial sequence
<220> FEATURE:
<223> OTHER INFORMATION: Synthetic peptide

<400> SEQUENCE: 16

Cys Asn Asp Ser Leu Asn Thr Gly Phe Leu Ala Ser Leu Phe Tyr Thr
1               5                   10                  15

His

<210> SEQ ID NO 17
<211> LENGTH: 17
<212> TYPE: PRT
<213> ORGANISM: Artificial sequence
<220> FEATURE:
<223> OTHER INFORMATION: Synthetic peptide

<400> SEQUENCE: 17

Cys Asn Asp Ser Leu Gln Thr Gly Phe Ile Ala Gly Leu Met Tyr Ala
1               5                   10                  15

His

<210> SEQ ID NO 18
<211> LENGTH: 17
<212> TYPE: PRT
<213> ORGANISM: Artificial sequence
<220> FEATURE:
<223> OTHER INFORMATION: Synthetic peptide

<400> SEQUENCE: 18

Cys Asn Asp Ser Leu Gln Thr Gly Phe Leu Ala Ser Leu Phe Tyr Thr
1               5                   10                  15

His

<210> SEQ ID NO 19
<211> LENGTH: 34
<212> TYPE: PRT
<213> ORGANISM: Artificial sequence
<220> FEATURE:
<223> OTHER INFORMATION: Synthetic peptide

<400> SEQUENCE: 19

Tyr Ser Trp Gly Glu Asn Glu Thr Asp Val Met Leu Leu Asn Asn Thr
1               5                   10                  15

Arg Pro Pro Gln Gly Asn Trp Phe Gly Cys Thr Trp Met Asn Ser Thr
                20                  25                  30

Gly Phe

<210> SEQ ID NO 20
<211> LENGTH: 34
<212> TYPE: PRT
<213> ORGANISM: Artificial sequence
<220> FEATURE:
<223> OTHER INFORMATION: Synthetic peptide

```
<400> SEQUENCE: 20

Tyr Thr Trp Gly Glu Asn Glu Thr Asp Val Phe Ile Leu Asn Ser Thr
1               5                   10                  15

Arg Pro Pro Gly Gly Ser Trp Phe Gly Cys Thr Trp Met Asn Ser Thr
            20                  25                  30

Gly Phe

<210> SEQ ID NO 21
<211> LENGTH: 34
<212> TYPE: PRT
<213> ORGANISM: Artificial sequence
<220> FEATURE:
<223> OTHER INFORMATION: Synthetic peptide

<400> SEQUENCE: 21

Tyr Arg Phe Gly Val Asn Glu Ser Asp Val Phe Leu Leu Thr Ser Leu
1               5                   10                  15

Arg Pro Pro Gln Gly Arg Trp Phe Gly Cys Val Trp Met Asn Ser Thr
            20                  25                  30

Gly Phe

<210> SEQ ID NO 22
<211> LENGTH: 34
<212> TYPE: PRT
<213> ORGANISM: Artificial sequence
<220> FEATURE:
<223> OTHER INFORMATION: Synthetic peptide

<400> SEQUENCE: 22

Tyr Thr Trp Gly Glu Asn Glu Thr Asp Val Phe Leu Leu Asn Ser Thr
1               5                   10                  15

Arg Pro Pro His Gly Ala Trp Phe Gly Cys Val Trp Met Asn Ser Thr
            20                  25                  30

Gly Phe

<210> SEQ ID NO 23
<211> LENGTH: 34
<212> TYPE: PRT
<213> ORGANISM: Artificial sequence
<220> FEATURE:
<223> OTHER INFORMATION: Synthetic peptide

<400> SEQUENCE: 23

Tyr Asn Trp Gly Ser Asn Glu Thr Asp Ile Leu Leu Leu Asn Asn Ile
1               5                   10                  15

Arg Pro Pro Ala Gly Asn Trp Phe Gly Cys Thr Trp Met Asn Ser Thr
            20                  25                  30

Gly Phe

<210> SEQ ID NO 24
<211> LENGTH: 34
<212> TYPE: PRT
<213> ORGANISM: Artificial sequence
<220> FEATURE:
<223> OTHER INFORMATION: Synthetic peptide

<400> SEQUENCE: 24

Tyr Thr Trp Gly Glu Asn Glu Thr Asp Val Phe Met Leu Glu Ser Leu
1               5                   10                  15

Arg Pro Pro Thr Gly Gly Trp Phe Gly Cys Thr Trp Met Asn Ser Thr
            20                  25                  30
```

Gly Phe

<210> SEQ ID NO 25
<211> LENGTH: 27
<212> TYPE: PRT
<213> ORGANISM: Artificial sequence
<220> FEATURE:
<223> OTHER INFORMATION: Synthetic peptide

<400> SEQUENCE: 25

Asp Tyr Pro Tyr Arg Leu Trp His Tyr Pro Cys Thr Leu Asn Phe Ser
1               5                   10                  15

Ile Phe Lys Val Arg Met Tyr Val Gly Gly Val
            20                  25

<210> SEQ ID NO 26
<211> LENGTH: 27
<212> TYPE: PRT
<213> ORGANISM: Artificial sequence
<220> FEATURE:
<223> OTHER INFORMATION: Synthetic peptide

<400> SEQUENCE: 26

Asp Tyr Pro Tyr Arg Leu Trp His Tyr Pro Cys Thr Ile Asn Tyr Thr
1               5                   10                  15

Ile Phe Lys Ile Arg Met Tyr Val Gly Gly Val
            20                  25

<210> SEQ ID NO 27
<211> LENGTH: 27
<212> TYPE: PRT
<213> ORGANISM: Artificial sequence
<220> FEATURE:
<223> OTHER INFORMATION: Synthetic peptide

<400> SEQUENCE: 27

Asp Tyr Pro Tyr Arg Leu Trp His Tyr Pro Cys Thr Val Asn Phe Ser
1               5                   10                  15

Ile Phe Lys Val Arg Met Phe Val Gly Gly His
            20                  25

<210> SEQ ID NO 28
<211> LENGTH: 27
<212> TYPE: PRT
<213> ORGANISM: Artificial sequence
<220> FEATURE:
<223> OTHER INFORMATION: Synthetic peptide

<400> SEQUENCE: 28

Asp Tyr Pro Tyr Arg Leu Trp His Phe Pro Cys Thr Ala Asn Phe Ser
1               5                   10                  15

Val Phe Asn Ile Arg Thr Phe Val Gly Gly Ile
            20                  25

<210> SEQ ID NO 29
<211> LENGTH: 27
<212> TYPE: PRT
<213> ORGANISM: Artificial sequence
<220> FEATURE:
<223> OTHER INFORMATION: Synthetic peptide

<400> SEQUENCE: 29

His Tyr Pro Tyr Arg Leu Trp His Tyr Pro Cys Thr Val Asn Tyr Thr
1               5                   10                  15

```
Ile Phe Lys Val Arg Met Phe Ile Gly Gly Leu
            20                  25
```

<210> SEQ ID NO 30
<211> LENGTH: 27
<212> TYPE: PRT
<213> ORGANISM: Artificial sequence
<220> FEATURE:
<223> OTHER INFORMATION: Synthetic peptide

<400> SEQUENCE: 30

```
Asp Tyr Ala Tyr Arg Leu Trp His Tyr Pro Cys Thr Val Asn Phe Thr
1               5                   10                  15

Leu His Lys Val Arg Met Phe Val Gly Gly Thr
            20                  25
```

<210> SEQ ID NO 31
<211> LENGTH: 35
<212> TYPE: PRT
<213> ORGANISM: Artificial sequence
<220> FEATURE:
<223> OTHER INFORMATION: Synthetic peptide

<400> SEQUENCE: 31

```
Ala Leu Ser Thr Gly Leu Ile His Leu His Gln Asn Ile Val Asp Val
1               5                   10                  15

Gln Tyr Leu Tyr Gly Val Gly Ser Ala Phe Val Ser Phe Ala Ile Lys
            20                  25                  30

Trp Glu Tyr
        35
```

<210> SEQ ID NO 32
<211> LENGTH: 35
<212> TYPE: PRT
<213> ORGANISM: Artificial sequence
<220> FEATURE:
<223> OTHER INFORMATION: Synthetic peptide

<400> SEQUENCE: 32

```
Ala Leu Ser Thr Gly Leu Leu His Leu His Gln Asn Ile Val Asp Val
1               5                   10                  15

Gln Tyr Met Tyr Gly Leu Ser Pro Ala Leu Thr Lys Tyr Ile Val Arg
            20                  25                  30

Trp Glu Trp
        35
```

<210> SEQ ID NO 33
<211> LENGTH: 35
<212> TYPE: PRT
<213> ORGANISM: Artificial sequence
<220> FEATURE:
<223> OTHER INFORMATION: Synthetic peptide

<400> SEQUENCE: 33

```
Arg Leu Ser Thr Gly Leu Ile His Leu His Gln Asn Ile Val Asp Val
1               5                   10                  15

Gln Tyr Leu Tyr Gly Val Gly Ser Ala Val Val Gly Trp Ala Leu Lys
            20                  25                  30

Trp Glu Phe
        35
```

<210> SEQ ID NO 34

```
<211> LENGTH: 35
<212> TYPE: PRT
<213> ORGANISM: Artificial sequence
<220> FEATURE:
<223> OTHER INFORMATION: Synthetic peptide

<400> SEQUENCE: 34

Ala Leu Ser Thr Gly Leu Ile His Leu His Gln Asn Ile Val Asp Val
1               5                   10                  15

Gln Tyr Leu Tyr Gly Val Gly Ser Ala Val Val Ser Trp Ala Leu Lys
            20                  25                  30

Trp Glu Tyr
        35

<210> SEQ ID NO 35
<211> LENGTH: 35
<212> TYPE: PRT
<213> ORGANISM: Artificial sequence
<220> FEATURE:
<223> OTHER INFORMATION: Synthetic peptide

<400> SEQUENCE: 35

Ala Leu Ser Thr Gly Leu Ile His Leu His Gln Asn Ile Val Asp Thr
1               5                   10                  15

Gln Tyr Leu Tyr Gly Leu Ser Ser Ser Ile Val Ser Trp Ala Val Lys
            20                  25                  30

Trp Glu Tyr
        35

<210> SEQ ID NO 36
<211> LENGTH: 35
<212> TYPE: PRT
<213> ORGANISM: Artificial sequence
<220> FEATURE:
<223> OTHER INFORMATION: Synthetic peptide

<400> SEQUENCE: 36

Ala Leu Ser Thr Gly Leu Ile His Leu His Gln Asn Ile Val Asp Val
1               5                   10                  15

Gln Tyr Leu Tyr Gly Val Ser Thr Asn Val Thr Ser Trp Val Val Lys
            20                  25                  30

Trp Glu Tyr
        35

<210> SEQ ID NO 37
<211> LENGTH: 28
<212> TYPE: PRT
<213> ORGANISM: Artificial sequence
<220> FEATURE:
<223> OTHER INFORMATION: Synthetic peptide

<400> SEQUENCE: 37

Ile Leu Leu Leu Phe Leu Leu Leu Ala Asp Ala Arg Val Cys Ala Cys
1               5                   10                  15

Leu Trp Met Met Leu Leu Ile Ala Gln Ala Glu Ala
            20                  25

<210> SEQ ID NO 38
<211> LENGTH: 28
<212> TYPE: PRT
<213> ORGANISM: Artificial sequence
<220> FEATURE:
<223> OTHER INFORMATION: Synthetic peptide
```

```
<400> SEQUENCE: 38

Val Val Leu Leu Phe Leu Leu Leu Ala Asp Ala Arg Val Cys Ala Cys
1               5                   10                  15

Leu Trp Met Leu Ile Leu Leu Gly Gln Ala Glu Ala
            20                  25

<210> SEQ ID NO 39
<211> LENGTH: 28
<212> TYPE: PRT
<213> ORGANISM: Artificial sequence
<220> FEATURE:
<223> OTHER INFORMATION: Synthetic peptide

<400> SEQUENCE: 39

Val Val Leu Val Phe Leu Leu Leu Ala Asp Ala Arg Val Cys Val Ala
1               5                   10                  15

Leu Trp Met Met Leu Leu Ile Ser Gln Ala Glu Ala
            20                  25

<210> SEQ ID NO 40
<211> LENGTH: 28
<212> TYPE: PRT
<213> ORGANISM: Artificial sequence
<220> FEATURE:
<223> OTHER INFORMATION: Synthetic peptide

<400> SEQUENCE: 40

Val Val Leu Ala Phe Leu Leu Leu Ala Asp Ala Arg Val Ser Ala Tyr
1               5                   10                  15

Leu Trp Met Met Phe Met Val Ser Gln Val Glu Ala
            20                  25

<210> SEQ ID NO 41
<211> LENGTH: 28
<212> TYPE: PRT
<213> ORGANISM: Artificial sequence
<220> FEATURE:
<223> OTHER INFORMATION: Synthetic peptide

<400> SEQUENCE: 41

Ile Met Leu Val Phe Leu Leu Leu Ala Asp Ala Arg Ile Cys Thr Cys
1               5                   10                  15

Leu Leu Ile Leu Leu Leu Ile Cys Gln Ala Glu Ala
            20                  25

<210> SEQ ID NO 42
<211> LENGTH: 28
<212> TYPE: PRT
<213> ORGANISM: Artificial sequence
<220> FEATURE:
<223> OTHER INFORMATION: Synthetic peptide

<400> SEQUENCE: 42

Ile Val Leu Met Phe Leu Val Leu Ala Asp Ala Arg Ile Cys Thr Cys
1               5                   10                  15

Leu Trp Leu Met Leu Leu Ile Ser Thr Val Glu Ala
            20                  25

<210> SEQ ID NO 43
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 43

Ala Gly Val Asp Ala Glu Thr His Val Thr Gly Gly Ser Ala Gly Arg
1               5                   10                  15

Thr Thr

<210> SEQ ID NO 44
<211> LENGTH: 18
<212> TYPE: PRT
<213> ORGANISM: Artificial sequence
<220> FEATURE:
<223> OTHER INFORMATION: Synthetic peptide

<400> SEQUENCE: 44

His Val Thr Gly Gly Ser Ala Gly Arg Thr Thr Ala Gly Leu Val Gly
1               5                   10                  15

Leu Leu

<210> SEQ ID NO 45
<211> LENGTH: 18
<212> TYPE: PRT
<213> ORGANISM: Artificial sequence
<220> FEATURE:
<223> OTHER INFORMATION: Synthetic peptide

<400> SEQUENCE: 45

Gly Arg Thr Thr Ala Gly Leu Val Gly Leu Leu Thr Pro Gly Ala Lys
1               5                   10                  15

Gln Asn

<210> SEQ ID NO 46
<211> LENGTH: 18
<212> TYPE: PRT
<213> ORGANISM: Artificial sequence
<220> FEATURE:
<223> OTHER INFORMATION: Synthetic peptide

<400> SEQUENCE: 46

Val Gly Leu Leu Thr Pro Gly Ala Lys Gln Asn Ile Gln Leu Ile Asn
1               5                   10                  15

Thr Asn

<210> SEQ ID NO 47
<211> LENGTH: 18
<212> TYPE: PRT
<213> ORGANISM: Artificial sequence
<220> FEATURE:
<223> OTHER INFORMATION: Synthetic peptide

<400> SEQUENCE: 47

Ala Lys Gln Asn Ile Gln Leu Ile Asn Thr Asn Gly Ser Trp His Ile
1               5                   10                  15

Asn Ser

<210> SEQ ID NO 48
<211> LENGTH: 18
<212> TYPE: PRT
<213> ORGANISM: Artificial sequence
<220> FEATURE:
<223> OTHER INFORMATION: Synthetic peptide

<400> SEQUENCE: 48

Ile Asn Thr Asn Gly Ser Trp His Ile Asn Ser Thr Ala Leu Asn Cys
```

-continued

```
              1               5                  10                  15
Asn Glu

<210> SEQ ID NO 49
<211> LENGTH: 18
<212> TYPE: PRT
<213> ORGANISM: Artificial sequence
<220> FEATURE:
<223> OTHER INFORMATION: Synthetic peptide

<400> SEQUENCE: 49

His Ile Asn Ser Thr Ala Leu Asn Cys Asn Glu Ser Leu Asn Thr Gly
1               5                  10                  15

Trp Leu

<210> SEQ ID NO 50
<211> LENGTH: 18
<212> TYPE: PRT
<213> ORGANISM: Artificial sequence
<220> FEATURE:
<223> OTHER INFORMATION: Synthetic peptide

<400> SEQUENCE: 50

Asn Cys Asn Glu Ser Leu Asn Thr Gly Trp Leu Ala Gly Leu Phe Tyr
1               5                  10                  15

Gln His

<210> SEQ ID NO 51
<211> LENGTH: 18
<212> TYPE: PRT
<213> ORGANISM: Artificial sequence
<220> FEATURE:
<223> OTHER INFORMATION: Synthetic peptide

<400> SEQUENCE: 51

Phe Tyr Gln His Lys Phe Asn Ser Ser Gly Cys Pro Glu Arg Leu Ala
1               5                  10                  15

Ser Cys

<210> SEQ ID NO 52
<211> LENGTH: 18
<212> TYPE: PRT
<213> ORGANISM: Artificial sequence
<220> FEATURE:
<223> OTHER INFORMATION: Synthetic peptide

<400> SEQUENCE: 52

Ser Ser Gly Cys Pro Glu Arg Leu Ala Ser Cys Arg Arg Leu Thr Asp
1               5                  10                  15

Phe Ala

<210> SEQ ID NO 53
<211> LENGTH: 18
<212> TYPE: PRT
<213> ORGANISM: Artificial sequence
<220> FEATURE:
<223> OTHER INFORMATION: Synthetic peptide

<400> SEQUENCE: 53

Leu Ala Ser Cys Arg Arg Leu Thr Asp Phe Ala Gln Gly Trp Gly Pro
1               5                  10                  15

Ile Ser
```

<210> SEQ ID NO 54
<211> LENGTH: 18
<212> TYPE: PRT
<213> ORGANISM: Artificial sequence
<220> FEATURE:
<223> OTHER INFORMATION: Synthetic peptide

<400> SEQUENCE: 54

Thr Asp Phe Ala Gln Gly Trp Gly Pro Ile Ser Tyr Ala Asn Gly Ser
1               5                   10                  15

Gly Leu

<210> SEQ ID NO 55
<211> LENGTH: 18
<212> TYPE: PRT
<213> ORGANISM: Artificial sequence
<220> FEATURE:
<223> OTHER INFORMATION: Synthetic peptide

<400> SEQUENCE: 55

Gly Pro Ile Ser Tyr Ala Asn Gly Ser Gly Leu Asp Glu Arg Pro Tyr
1               5                   10                  15

Cys Trp

<210> SEQ ID NO 56
<211> LENGTH: 18
<212> TYPE: PRT
<213> ORGANISM: Artificial sequence
<220> FEATURE:
<223> OTHER INFORMATION: Synthetic peptide

<400> SEQUENCE: 56

Gly Ser Gly Leu Asp Glu Arg Pro Tyr Cys Trp His Tyr Pro Pro Arg
1               5                   10                  15

Pro Cys

<210> SEQ ID NO 57
<211> LENGTH: 18
<212> TYPE: PRT
<213> ORGANISM: Artificial sequence
<220> FEATURE:
<223> OTHER INFORMATION: Synthetic peptide

<400> SEQUENCE: 57

Pro Tyr Cys Trp His Tyr Pro Pro Arg Pro Cys Gly Ile Val Pro Ala
1               5                   10                  15

Lys Ser

<210> SEQ ID NO 58
<211> LENGTH: 18
<212> TYPE: PRT
<213> ORGANISM: Artificial sequence
<220> FEATURE:
<223> OTHER INFORMATION: Synthetic peptide

<400> SEQUENCE: 58

Pro Arg Pro Cys Gly Ile Val Pro Ala Lys Ser Val Cys Gly Pro Val
1               5                   10                  15

Tyr Cys

<210> SEQ ID NO 59
<211> LENGTH: 18
<212> TYPE: PRT

<213> ORGANISM: Artificial sequence
<220> FEATURE:
<223> OTHER INFORMATION: Synthetic peptide

<400> SEQUENCE: 59

Pro Ala Lys Ser Val Cys Gly Pro Val Tyr Cys Phe Thr Pro Ser Pro
1               5                   10                  15

Val Val

<210> SEQ ID NO 60
<211> LENGTH: 18
<212> TYPE: PRT
<213> ORGANISM: Artificial sequence
<220> FEATURE:
<223> OTHER INFORMATION: Synthetic peptide

<400> SEQUENCE: 60

Pro Val Tyr Cys Phe Thr Pro Ser Pro Val Val Val Gly Thr Thr Asp
1               5                   10                  15

Arg Ser

<210> SEQ ID NO 61
<211> LENGTH: 18
<212> TYPE: PRT
<213> ORGANISM: Artificial sequence
<220> FEATURE:
<223> OTHER INFORMATION: Synthetic peptide

<400> SEQUENCE: 61

Ser Pro Val Val Val Gly Thr Thr Asp Arg Ser Gly Ala Pro Thr Tyr
1               5                   10                  15

Ser Trp

<210> SEQ ID NO 62
<211> LENGTH: 18
<212> TYPE: PRT
<213> ORGANISM: Artificial sequence
<220> FEATURE:
<223> OTHER INFORMATION: Synthetic peptide

<400> SEQUENCE: 62

Thr Tyr Ser Trp Gly Ala Asn Asp Thr Asp Val Phe Val Leu Asn Asn
1               5                   10                  15

Thr Arg

<210> SEQ ID NO 63
<211> LENGTH: 18
<212> TYPE: PRT
<213> ORGANISM: Artificial sequence
<220> FEATURE:
<223> OTHER INFORMATION: Synthetic peptide

<400> SEQUENCE: 63

Asp Thr Asp Val Phe Val Leu Asn Asn Thr Arg Pro Pro Leu Gly Asn
1               5                   10                  15

Trp Phe

<210> SEQ ID NO 64
<211> LENGTH: 18
<212> TYPE: PRT
<213> ORGANISM: Artificial sequence
<220> FEATURE:
<223> OTHER INFORMATION: Synthetic peptide

```
<400> SEQUENCE: 64

Asn Asn Thr Arg Pro Pro Leu Gly Asn Trp Phe Gly Cys Thr Trp Met
1               5                   10                  15

Asn Ser

<210> SEQ ID NO 65
<211> LENGTH: 18
<212> TYPE: PRT
<213> ORGANISM: Artificial sequence
<220> FEATURE:
<223> OTHER INFORMATION: Synthetic peptide

<400> SEQUENCE: 65

Gly Asn Trp Phe Gly Cys Thr Trp Met Asn Ser Thr Gly Phe Thr Lys
1               5                   10                  15

Val Cys

<210> SEQ ID NO 66
<211> LENGTH: 18
<212> TYPE: PRT
<213> ORGANISM: Artificial sequence
<220> FEATURE:
<223> OTHER INFORMATION: Synthetic peptide

<400> SEQUENCE: 66

Trp Met Asn Ser Thr Gly Phe Thr Lys Val Cys Gly Ala Pro Pro Cys
1               5                   10                  15

Val Ile

<210> SEQ ID NO 67
<211> LENGTH: 18
<212> TYPE: PRT
<213> ORGANISM: Artificial sequence
<220> FEATURE:
<223> OTHER INFORMATION: Synthetic peptide

<400> SEQUENCE: 67

Thr Lys Val Cys Gly Ala Pro Pro Cys Val Ile Gly Gly Val Gly Asn
1               5                   10                  15

Asn Thr

<210> SEQ ID NO 68
<211> LENGTH: 18
<212> TYPE: PRT
<213> ORGANISM: Artificial sequence
<220> FEATURE:
<223> OTHER INFORMATION: Synthetic peptide

<400> SEQUENCE: 68

Pro Cys Val Ile Gly Gly Val Gly Asn Asn Thr Leu Leu Cys Pro Thr
1               5                   10                  15

Asp Cys

<210> SEQ ID NO 69
<211> LENGTH: 18
<212> TYPE: PRT
<213> ORGANISM: Artificial sequence
<220> FEATURE:
<223> OTHER INFORMATION: Synthetic peptide

<400> SEQUENCE: 69

Gly Asn Asn Thr Leu Leu Cys Pro Thr Asp Cys Phe Arg Lys His Pro
1               5                   10                  15
```

Glu Ala

<210> SEQ ID NO 70
<211> LENGTH: 18
<212> TYPE: PRT
<213> ORGANISM: Artificial sequence
<220> FEATURE:
<223> OTHER INFORMATION: Synthetic peptide

<400> SEQUENCE: 70

Pro Thr Asp Cys Phe Arg Lys His Pro Glu Ala Thr Tyr Ser Arg Cys
1               5                   10                  15

Gly Ser

<210> SEQ ID NO 71
<211> LENGTH: 18
<212> TYPE: PRT
<213> ORGANISM: Artificial sequence
<220> FEATURE:
<223> OTHER INFORMATION: Synthetic peptide

<400> SEQUENCE: 71

His Pro Glu Ala Thr Tyr Ser Arg Cys Gly Ser Gly Pro Trp Ile Thr
1               5                   10                  15

Pro Arg

<210> SEQ ID NO 72
<211> LENGTH: 18
<212> TYPE: PRT
<213> ORGANISM: Artificial sequence
<220> FEATURE:
<223> OTHER INFORMATION: Synthetic peptide

<400> SEQUENCE: 72

Arg Cys Gly Ser Gly Pro Trp Ile Thr Pro Arg Cys Met Val Asp Tyr
1               5                   10                  15

Pro Tyr

<210> SEQ ID NO 73
<211> LENGTH: 18
<212> TYPE: PRT
<213> ORGANISM: Artificial sequence
<220> FEATURE:
<223> OTHER INFORMATION: Synthetic peptide

<400> SEQUENCE: 73

Ile Thr Pro Arg Cys Met Val Asp Tyr Pro Tyr Arg Leu Trp His Tyr
1               5                   10                  15

Pro Cys

<210> SEQ ID NO 74
<211> LENGTH: 18
<212> TYPE: PRT
<213> ORGANISM: Artificial sequence
<220> FEATURE:
<223> OTHER INFORMATION: Synthetic peptide

<400> SEQUENCE: 74

Asp Tyr Pro Tyr Arg Leu Trp His Tyr Pro Cys Thr Ile Asn Tyr Thr
1               5                   10                  15

Ile Phe

```
<210> SEQ ID NO 75
<211> LENGTH: 18
<212> TYPE: PRT
<213> ORGANISM: Artificial sequence
<220> FEATURE:
<223> OTHER INFORMATION: Synthetic peptide

<400> SEQUENCE: 75

His Tyr Pro Cys Thr Ile Asn Tyr Thr Ile Phe Lys Val Arg Met Tyr
1               5                   10                  15

Val Gly

<210> SEQ ID NO 76
<211> LENGTH: 18
<212> TYPE: PRT
<213> ORGANISM: Artificial sequence
<220> FEATURE:
<223> OTHER INFORMATION: Synthetic peptide

<400> SEQUENCE: 76

Tyr Thr Ile Phe Lys Val Arg Met Tyr Val Gly Gly Val Glu His Arg
1               5                   10                  15

Leu Glu

<210> SEQ ID NO 77
<211> LENGTH: 18
<212> TYPE: PRT
<213> ORGANISM: Artificial sequence
<220> FEATURE:
<223> OTHER INFORMATION: Synthetic peptide

<400> SEQUENCE: 77

Met Tyr Val Gly Gly Val Glu His Arg Leu Glu Ala Ala Cys Asn Trp
1               5                   10                  15

Thr Arg

<210> SEQ ID NO 78
<211> LENGTH: 18
<212> TYPE: PRT
<213> ORGANISM: Artificial sequence
<220> FEATURE:
<223> OTHER INFORMATION: Synthetic peptide

<400> SEQUENCE: 78

His Arg Leu Glu Ala Ala Cys Asn Trp Thr Arg Gly Glu Arg Cys Asp
1               5                   10                  15

Leu Glu

<210> SEQ ID NO 79
<211> LENGTH: 18
<212> TYPE: PRT
<213> ORGANISM: Artificial sequence
<220> FEATURE:
<223> OTHER INFORMATION: Synthetic peptide

<400> SEQUENCE: 79

Asn Trp Thr Arg Gly Glu Arg Cys Asp Leu Glu Asp Arg Asp Arg Ser
1               5                   10                  15

Glu Leu

<210> SEQ ID NO 80
<211> LENGTH: 18
<212> TYPE: PRT
<213> ORGANISM: Artificial sequence
```

-continued

<220> FEATURE:
<223> OTHER INFORMATION: Synthetic peptide

<400> SEQUENCE: 80

Cys Asp Leu Glu Asp Arg Asp Arg Ser Glu Leu Ser Pro Leu Leu Leu
1               5                   10                  15

Ser Thr

<210> SEQ ID NO 81
<211> LENGTH: 18
<212> TYPE: PRT
<213> ORGANISM: Artificial sequence
<220> FEATURE:
<223> OTHER INFORMATION: Synthetic peptide

<400> SEQUENCE: 81

Arg Ser Glu Leu Ser Pro Leu Leu Leu Ser Thr Thr Gln Trp Gln Val
1               5                   10                  15

Leu Pro

<210> SEQ ID NO 82
<211> LENGTH: 18
<212> TYPE: PRT
<213> ORGANISM: Artificial sequence
<220> FEATURE:
<223> OTHER INFORMATION: Synthetic peptide

<400> SEQUENCE: 82

Leu Leu Ser Thr Thr Gln Trp Gln Val Leu Pro Cys Ser Phe Thr Thr
1               5                   10                  15

Leu Pro

<210> SEQ ID NO 83
<211> LENGTH: 18
<212> TYPE: PRT
<213> ORGANISM: Artificial sequence
<220> FEATURE:
<223> OTHER INFORMATION: Synthetic peptide

<400> SEQUENCE: 83

Gln Val Leu Pro Cys Ser Phe Thr Thr Leu Pro Ala Leu Ser Thr Gly
1               5                   10                  15

Leu Ile

<210> SEQ ID NO 84
<211> LENGTH: 18
<212> TYPE: PRT
<213> ORGANISM: Artificial sequence
<220> FEATURE:
<223> OTHER INFORMATION: Synthetic peptide

<400> SEQUENCE: 84

Thr Thr Leu Pro Ala Leu Ser Thr Gly Leu Ile His Leu His Gln Asn
1               5                   10                  15

Ile Val

<210> SEQ ID NO 85
<211> LENGTH: 18
<212> TYPE: PRT
<213> ORGANISM: Artificial sequence
<220> FEATURE:
<223> OTHER INFORMATION: Synthetic peptide

<400> SEQUENCE: 85

Thr Gly Leu Ile His Leu His Gln Asn Ile Val Asp Val Gln Tyr Leu
1               5                   10                  15

Tyr Gly

<210> SEQ ID NO 86
<211> LENGTH: 18
<212> TYPE: PRT
<213> ORGANISM: Artificial sequence
<220> FEATURE:
<223> OTHER INFORMATION: Synthetic peptide

<400> SEQUENCE: 86

Gln Asn Ile Val Asp Val Gln Tyr Leu Tyr Gly Val Gly Ser Ser Ile
1               5                   10                  15

Ala Ser

<210> SEQ ID NO 87
<211> LENGTH: 18
<212> TYPE: PRT
<213> ORGANISM: Artificial sequence
<220> FEATURE:
<223> OTHER INFORMATION: Synthetic peptide

<400> SEQUENCE: 87

Tyr Leu Tyr Gly Val Gly Ser Ser Ile Ala Ser Trp Ala Ile Lys Trp
1               5                   10                  15

Glu Tyr

<210> SEQ ID NO 88
<211> LENGTH: 18
<212> TYPE: PRT
<213> ORGANISM: Artificial sequence
<220> FEATURE:
<223> OTHER INFORMATION: Synthetic peptide

<400> SEQUENCE: 88

Ser Ile Ala Ser Trp Ala Ile Lys Trp Glu Tyr Val Val Leu Leu Phe
1               5                   10                  15

Leu Leu

<210> SEQ ID NO 89
<211> LENGTH: 18
<212> TYPE: PRT
<213> ORGANISM: Artificial sequence
<220> FEATURE:
<223> OTHER INFORMATION: Synthetic peptide

<400> SEQUENCE: 89

Lys Trp Glu Tyr Val Val Leu Leu Phe Leu Leu Leu Ala Asp Ala Arg
1               5                   10                  15

Val Cys

<210> SEQ ID NO 90
<211> LENGTH: 18
<212> TYPE: PRT
<213> ORGANISM: Artificial sequence
<220> FEATURE:
<223> OTHER INFORMATION: Synthetic peptide

<400> SEQUENCE: 90

Leu Phe Leu Leu Leu Ala Asp Ala Arg Val Cys Ser Cys Leu Trp Met
1               5                   10                  15

Met Leu

<210> SEQ ID NO 91
<211> LENGTH: 18
<212> TYPE: PRT
<213> ORGANISM: Artificial sequence
<220> FEATURE:
<223> OTHER INFORMATION: Synthetic peptide

<400> SEQUENCE: 91

Ala Arg Val Cys Ser Cys Leu Trp Met Met Leu Leu Ile Ser Gln Ala
1               5                   10                  15

Glu Ala

<210> SEQ ID NO 92
<211> LENGTH: 18
<212> TYPE: PRT
<213> ORGANISM: Artificial sequence
<220> FEATURE:
<223> OTHER INFORMATION: Synthetic peptide

<400> SEQUENCE: 92

Trp Met Met Leu Leu Ile Ser Gln Ala Glu Ala Ala Leu Glu Gln Leu
1               5                   10                  15

Val Ile

<210> SEQ ID NO 93
<211> LENGTH: 18
<212> TYPE: PRT
<213> ORGANISM: Artificial sequence
<220> FEATURE:
<223> OTHER INFORMATION: Synthetic peptide

<400> SEQUENCE: 93

Ala Gly Val Asp Gly Glu Thr His Thr Thr Gly Arg Val Ala Gly His
1               5                   10                  15

Thr Thr

<210> SEQ ID NO 94
<211> LENGTH: 18
<212> TYPE: PRT
<213> ORGANISM: Artificial sequence
<220> FEATURE:
<223> OTHER INFORMATION: Synthetic peptide

<400> SEQUENCE: 94

His Thr Thr Gly Arg Val Ala Gly His Thr Thr Ser Gly Phe Thr Ser
1               5                   10                  15

Leu Phe

<210> SEQ ID NO 95
<211> LENGTH: 18
<212> TYPE: PRT
<213> ORGANISM: Artificial sequence
<220> FEATURE:
<223> OTHER INFORMATION: Synthetic peptide

<400> SEQUENCE: 95

Gly His Thr Thr Ser Gly Phe Thr Ser Leu Phe Ser Ser Gly Ala Ser
1               5                   10                  15

Gln Lys

<210> SEQ ID NO 96

-continued

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 96

Thr Ser Leu Phe Ser Ser Gly Ala Ser Gln Lys Ile Gln Leu Val Asn
1               5                   10                  15

Thr Asn

<210> SEQ ID NO 97
<211> LENGTH: 18
<212> TYPE: PRT
<213> ORGANISM: Artificial sequence
<220> FEATURE:
<223> OTHER INFORMATION: Synthetic peptide

<400> SEQUENCE: 97

Ala Ser Gln Lys Ile Gln Leu Val Asn Thr Asn Gly Ser Trp His Ile
1               5                   10                  15

Asn Arg

<210> SEQ ID NO 98
<211> LENGTH: 18
<212> TYPE: PRT
<213> ORGANISM: Artificial sequence
<220> FEATURE:
<223> OTHER INFORMATION: Synthetic peptide

<400> SEQUENCE: 98

His Ile Asn Arg Thr Ala Leu Asn Cys Asn Asp Ser Leu Gln Thr Gly
1               5                   10                  15

Phe Phe

<210> SEQ ID NO 99
<211> LENGTH: 18
<212> TYPE: PRT
<213> ORGANISM: Artificial sequence
<220> FEATURE:
<223> OTHER INFORMATION: Synthetic peptide

<400> SEQUENCE: 99

Asn Cys Asn Asp Ser Leu Gln Thr Gly Phe Phe Ala Ala Leu Phe Tyr
1               5                   10                  15

Ala His

<210> SEQ ID NO 100
<211> LENGTH: 18
<212> TYPE: PRT
<213> ORGANISM: Artificial sequence
<220> FEATURE:
<223> OTHER INFORMATION: Synthetic peptide

<400> SEQUENCE: 100

Thr Gly Phe Phe Ala Ala Leu Phe Tyr Ala His Lys Phe Asn Ser Ser
1               5                   10                  15

Gly Cys

<210> SEQ ID NO 101
<211> LENGTH: 18
<212> TYPE: PRT
<213> ORGANISM: Artificial sequence
<220> FEATURE:
```

```
<223> OTHER INFORMATION: Synthetic peptide

<400> SEQUENCE: 101

Phe Tyr Ala His Lys Phe Asn Ser Ser Gly Cys Pro Glu Arg Met Ala
1               5                   10                  15

Ser Cys

<210> SEQ ID NO 102
<211> LENGTH: 18
<212> TYPE: PRT
<213> ORGANISM: Artificial sequence
<220> FEATURE:
<223> OTHER INFORMATION: Synthetic peptide

<400> SEQUENCE: 102

Ser Ser Gly Cys Pro Glu Arg Met Ala Ser Cys Arg Pro Ile Asp Trp
1               5                   10                  15

Phe Ala

<210> SEQ ID NO 103
<211> LENGTH: 18
<212> TYPE: PRT
<213> ORGANISM: Artificial sequence
<220> FEATURE:
<223> OTHER INFORMATION: Synthetic peptide

<400> SEQUENCE: 103

Met Ala Ser Cys Arg Pro Ile Asp Trp Phe Ala Gln Gly Trp Gly Pro
1               5                   10                  15

Ile Thr

<210> SEQ ID NO 104
<211> LENGTH: 18
<212> TYPE: PRT
<213> ORGANISM: Artificial sequence
<220> FEATURE:
<223> OTHER INFORMATION: Synthetic peptide

<400> SEQUENCE: 104

Asp Trp Phe Ala Gln Gly Trp Gly Pro Ile Thr Tyr Thr Lys Pro Asn
1               5                   10                  15

Ser Ser

<210> SEQ ID NO 105
<211> LENGTH: 18
<212> TYPE: PRT
<213> ORGANISM: Artificial sequence
<220> FEATURE:
<223> OTHER INFORMATION: Synthetic peptide

<400> SEQUENCE: 105

Pro Asn Ser Ser Asp Gln Arg Pro Tyr Cys Trp His Tyr Ala Pro Arg
1               5                   10                  15

Pro Cys

<210> SEQ ID NO 106
<211> LENGTH: 18
<212> TYPE: PRT
<213> ORGANISM: Artificial sequence
<220> FEATURE:
<223> OTHER INFORMATION: Synthetic peptide

<400> SEQUENCE: 106
```

```
Pro Tyr Cys Trp His Tyr Ala Pro Arg Pro Cys Gly Val Val Pro Ala
1               5                   10                  15

Ser Gln
```

<210> SEQ ID NO 107
<211> LENGTH: 18
<212> TYPE: PRT
<213> ORGANISM: Artificial sequence
<220> FEATURE:
<223> OTHER INFORMATION: Synthetic peptide

<400> SEQUENCE: 107

```
Pro Arg Pro Cys Gly Val Val Pro Ala Ser Gln Val Cys Gly Pro Val
1               5                   10                  15

Tyr Cys
```

<210> SEQ ID NO 108
<211> LENGTH: 18
<212> TYPE: PRT
<213> ORGANISM: Artificial sequence
<220> FEATURE:
<223> OTHER INFORMATION: Synthetic peptide

<400> SEQUENCE: 108

```
Pro Ala Ser Gln Val Cys Gly Pro Val Tyr Cys Phe Thr Pro Ser Pro
1               5                   10                  15

Val Val
```

<210> SEQ ID NO 109
<211> LENGTH: 18
<212> TYPE: PRT
<213> ORGANISM: Artificial sequence
<220> FEATURE:
<223> OTHER INFORMATION: Synthetic peptide

<400> SEQUENCE: 109

```
Pro Val Tyr Cys Phe Thr Pro Ser Pro Val Val Val Gly Thr Thr Asp
1               5                   10                  15

Arg Ser
```

<210> SEQ ID NO 110
<211> LENGTH: 18
<212> TYPE: PRT
<213> ORGANISM: Artificial sequence
<220> FEATURE:
<223> OTHER INFORMATION: Synthetic peptide

<400> SEQUENCE: 110

```
Ser Pro Val Val Val Gly Thr Thr Asp Arg Ser Gly Val Pro Thr Tyr
1               5                   10                  15

Ser Trp
```

<210> SEQ ID NO 111
<211> LENGTH: 18
<212> TYPE: PRT
<213> ORGANISM: Artificial sequence
<220> FEATURE:
<223> OTHER INFORMATION: Synthetic peptide

<400> SEQUENCE: 111

```
Thr Asp Arg Ser Gly Val Pro Thr Tyr Ser Trp Gly Glu Asn Glu Thr
1               5                   10                  15

Asp Val
```

<210> SEQ ID NO 112
<211> LENGTH: 18
<212> TYPE: PRT
<213> ORGANISM: Artificial sequence
<220> FEATURE:
<223> OTHER INFORMATION: Synthetic peptide

<400> SEQUENCE: 112

Thr Tyr Ser Trp Gly Glu Asn Glu Thr Asp Val Met Leu Leu Asn Asn
1               5                   10                  15

Thr Arg

<210> SEQ ID NO 113
<211> LENGTH: 18
<212> TYPE: PRT
<213> ORGANISM: Artificial sequence
<220> FEATURE:
<223> OTHER INFORMATION: Synthetic peptide

<400> SEQUENCE: 113

Glu Thr Asp Val Met Leu Leu Asn Asn Thr Arg Pro Pro Gln Gly Asn
1               5                   10                  15

Trp Phe

<210> SEQ ID NO 114
<211> LENGTH: 18
<212> TYPE: PRT
<213> ORGANISM: Artificial sequence
<220> FEATURE:
<223> OTHER INFORMATION: Synthetic peptide

<400> SEQUENCE: 114

Asn Asn Thr Arg Pro Pro Gln Gly Asn Trp Phe Gly Cys Thr Trp Met
1               5                   10                  15

Asn Ser

<210> SEQ ID NO 115
<211> LENGTH: 18
<212> TYPE: PRT
<213> ORGANISM: Artificial sequence
<220> FEATURE:
<223> OTHER INFORMATION: Synthetic peptide

<400> SEQUENCE: 115

Trp Met Asn Ser Thr Gly Phe Thr Lys Thr Cys Gly Gly Pro Pro Cys
1               5                   10                  15

Asn Ile

<210> SEQ ID NO 116
<211> LENGTH: 18
<212> TYPE: PRT
<213> ORGANISM: Artificial sequence
<220> FEATURE:
<223> OTHER INFORMATION: Synthetic peptide

<400> SEQUENCE: 116

Thr Lys Thr Cys Gly Gly Pro Pro Cys Asn Ile Gly Gly Val Gly Asn
1               5                   10                  15

Arg Thr

<210> SEQ ID NO 117
<211> LENGTH: 18

<212> TYPE: PRT
<213> ORGANISM: Artificial sequence
<220> FEATURE:
<223> OTHER INFORMATION: Synthetic peptide

<400> SEQUENCE: 117

Pro Cys Asn Ile Gly Gly Val Gly Asn Arg Thr Leu Ile Cys Pro Thr
1               5                   10                  15
Asp Cys

<210> SEQ ID NO 118
<211> LENGTH: 18
<212> TYPE: PRT
<213> ORGANISM: Artificial sequence
<220> FEATURE:
<223> OTHER INFORMATION: Synthetic peptide

<400> SEQUENCE: 118

Gly Asn Arg Thr Leu Ile Cys Pro Thr Asp Cys Phe Arg Lys His Pro
1               5                   10                  15
Glu Ala

<210> SEQ ID NO 119
<211> LENGTH: 18
<212> TYPE: PRT
<213> ORGANISM: Artificial sequence
<220> FEATURE:
<223> OTHER INFORMATION: Synthetic peptide

<400> SEQUENCE: 119

Pro Thr Asp Cys Phe Arg Lys His Pro Glu Ala Thr Tyr Thr Lys Cys
1               5                   10                  15
Gly Ser

<210> SEQ ID NO 120
<211> LENGTH: 18
<212> TYPE: PRT
<213> ORGANISM: Artificial sequence
<220> FEATURE:
<223> OTHER INFORMATION: Synthetic peptide

<400> SEQUENCE: 120

His Pro Glu Ala Thr Tyr Thr Lys Cys Gly Ser Gly Pro Trp Leu Thr
1               5                   10                  15
Pro Arg

<210> SEQ ID NO 121
<211> LENGTH: 18
<212> TYPE: PRT
<213> ORGANISM: Artificial sequence
<220> FEATURE:
<223> OTHER INFORMATION: Synthetic peptide

<400> SEQUENCE: 121

Lys Cys Gly Ser Gly Pro Trp Leu Thr Pro Arg Cys Leu Val Asp Tyr
1               5                   10                  15
Pro Tyr

<210> SEQ ID NO 122
<211> LENGTH: 18
<212> TYPE: PRT
<213> ORGANISM: Artificial sequence
<220> FEATURE:
<223> OTHER INFORMATION: Synthetic peptide

<400> SEQUENCE: 122

Leu Thr Pro Arg Cys Leu Val Asp Tyr Pro Tyr Arg Leu Trp His Tyr
1               5                   10                  15
Pro Cys

<210> SEQ ID NO 123
<211> LENGTH: 18
<212> TYPE: PRT
<213> ORGANISM: Artificial sequence
<220> FEATURE:
<223> OTHER INFORMATION: Synthetic peptide

<400> SEQUENCE: 123

Asp Tyr Pro Tyr Arg Leu Trp His Tyr Pro Cys Thr Leu Asn Phe Ser
1               5                   10                  15
Ile Phe

<210> SEQ ID NO 124
<211> LENGTH: 18
<212> TYPE: PRT
<213> ORGANISM: Artificial sequence
<220> FEATURE:
<223> OTHER INFORMATION: Synthetic peptide

<400> SEQUENCE: 124

His Tyr Pro Cys Thr Leu Asn Phe Ser Ile Phe Lys Val Arg Met Tyr
1               5                   10                  15
Val Gly

<210> SEQ ID NO 125
<211> LENGTH: 18
<212> TYPE: PRT
<213> ORGANISM: Artificial sequence
<220> FEATURE:
<223> OTHER INFORMATION: Synthetic peptide

<400> SEQUENCE: 125

Met Tyr Val Gly Gly Val Glu His Arg Leu Asn Ala Ala Cys Asn Trp
1               5                   10                  15
Thr Arg

<210> SEQ ID NO 126
<211> LENGTH: 18
<212> TYPE: PRT
<213> ORGANISM: Artificial sequence
<220> FEATURE:
<223> OTHER INFORMATION: Synthetic peptide

<400> SEQUENCE: 126

His Arg Leu Asn Ala Ala Cys Asn Trp Thr Arg Gly Glu Arg Cys Asn
1               5                   10                  15
Leu Glu

<210> SEQ ID NO 127
<211> LENGTH: 18
<212> TYPE: PRT
<213> ORGANISM: Artificial sequence
<220> FEATURE:
<223> OTHER INFORMATION: Synthetic peptide

<400> SEQUENCE: 127

Asn Trp Thr Arg Gly Glu Arg Cys Asn Leu Glu Asp Arg Asp Arg Ser

-continued

```
1               5                   10                  15

Glu Leu

<210> SEQ ID NO 128
<211> LENGTH: 18
<212> TYPE: PRT
<213> ORGANISM: Artificial sequence
<220> FEATURE:
<223> OTHER INFORMATION: Synthetic peptide

<400> SEQUENCE: 128

Cys Asn Leu Glu Asp Arg Asp Arg Ser Glu Leu Ser Pro Leu Leu Leu
1               5                   10                  15

Ser Thr

<210> SEQ ID NO 129
<211> LENGTH: 18
<212> TYPE: PRT
<213> ORGANISM: Artificial sequence
<220> FEATURE:
<223> OTHER INFORMATION: Synthetic peptide

<400> SEQUENCE: 129

Arg Ser Glu Leu Ser Pro Leu Leu Leu Ser Thr Thr Glu Trp Gln Ile
1               5                   10                  15

Leu Pro

<210> SEQ ID NO 130
<211> LENGTH: 18
<212> TYPE: PRT
<213> ORGANISM: Artificial sequence
<220> FEATURE:
<223> OTHER INFORMATION: Synthetic peptide

<400> SEQUENCE: 130

Leu Leu Ser Thr Thr Glu Trp Gln Ile Leu Pro Cys Ala Phe Thr Thr
1               5                   10                  15

Leu Pro

<210> SEQ ID NO 131
<211> LENGTH: 18
<212> TYPE: PRT
<213> ORGANISM: Artificial sequence
<220> FEATURE:
<223> OTHER INFORMATION: Synthetic peptide

<400> SEQUENCE: 131

Gln Ile Leu Pro Cys Ala Phe Thr Thr Leu Pro Ala Leu Ser Thr Gly
1               5                   10                  15

Leu Ile

<210> SEQ ID NO 132
<211> LENGTH: 18
<212> TYPE: PRT
<213> ORGANISM: Artificial sequence
<220> FEATURE:
<223> OTHER INFORMATION: Synthetic peptide

<400> SEQUENCE: 132

Thr Thr Leu Pro Ala Leu Ser Thr Gly Leu Ile His Leu His Gln Asn
1               5                   10                  15

Ile Val
```

<210> SEQ ID NO 133
<211> LENGTH: 18
<212> TYPE: PRT
<213> ORGANISM: Artificial sequence
<220> FEATURE:
<223> OTHER INFORMATION: Synthetic peptide

<400> SEQUENCE: 133

```
Gln Asn Ile Val Asp Val Gln Tyr Leu Tyr Gly Val Gly Ser Ala Phe
 1               5                  10                  15

Val Ser
```

<210> SEQ ID NO 134
<211> LENGTH: 18
<212> TYPE: PRT
<213> ORGANISM: Artificial sequence
<220> FEATURE:
<223> OTHER INFORMATION: Synthetic peptide

<400> SEQUENCE: 134

```
Ala Phe Val Ser Phe Ala Ile Lys Trp Glu Tyr Ile Leu Leu Leu Phe
 1               5                  10                  15

Leu Leu
```

<210> SEQ ID NO 135
<211> LENGTH: 18
<212> TYPE: PRT
<213> ORGANISM: Artificial sequence
<220> FEATURE:
<223> OTHER INFORMATION: Synthetic peptide

<400> SEQUENCE: 135

```
Leu Phe Leu Leu Leu Ala Asp Ala Arg Val Cys Ala Cys Leu Trp Met
 1               5                  10                  15

Met Leu
```

<210> SEQ ID NO 136
<211> LENGTH: 18
<212> TYPE: PRT
<213> ORGANISM: Artificial sequence
<220> FEATURE:
<223> OTHER INFORMATION: Synthetic peptide

<400> SEQUENCE: 136

```
Ala Arg Val Cys Ala Cys Leu Trp Met Met Leu Leu Ile Ala Gln Ala
 1               5                  10                  15

Glu Ala
```

<210> SEQ ID NO 137
<211> LENGTH: 360
<212> TYPE: PRT
<213> ORGANISM: Hepatitis C Virus

<400> SEQUENCE: 137

```
Glu Thr His Val Thr Gly Gly Asn Ala Gly Arg Thr Thr Ala Gly Leu
 1               5                  10                  15

Val Gly Leu Leu Thr Pro Gly Ala Lys Gln Asn Ile Gln Leu Ile Asn
                20                  25                  30

Thr Asn Gly Ser Trp His Ile Asn Ser Thr Ala Leu Asn Cys Asn Glu
            35                  40                  45

Ser Leu Asn Thr Gly Trp Leu Ala Gly Leu Phe Tyr Gln His Lys Phe
        50                  55                  60
```

```
Asn Ser Ser Gly Cys Pro Glu Arg Leu Thr Ser Cys Arg Arg Leu Thr
 65                  70                  75                  80

Asp Phe Ala Gln Gly Trp Gly Pro Ile Ser Tyr Ala Asn Gly Ser Gly
                 85                  90                  95

Leu Asp Glu Arg Pro Tyr Cys Trp His Tyr Pro Pro Arg Pro Cys Gly
                100                 105                 110

Ile Val Pro Ala Lys Ser Val Cys Gly Pro Val Tyr Cys Phe Thr Pro
                115                 120                 125

Ser Pro Val Val Val Gly Thr Thr Asp Arg Ser Gly Ala Pro Thr Tyr
130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
                180                 185                 190

Asn Asn Thr Leu Leu Cys Pro Thr Asp Cys Phe Arg Lys His Pro Glu
                195                 200                 205

Ala Thr Tyr Ser Arg Cys Gly Ser Gly Pro Trp Ile Thr Pro Arg Cys
210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Gln
                275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
                340                 345                 350

Trp Met Met Leu Leu Ile Ser Gln
                355                 360

<210> SEQ ID NO 138
<211> LENGTH: 360
<212> TYPE: PRT
<213> ORGANISM: Hepatitis C Virus

<400> SEQUENCE: 138

Ala Thr Tyr Thr Ser Gly Gly Val Ala Gly Arg Thr Thr Ser Gly Phe
1               5                   10                  15

Thr Ser Leu Phe Ser Ser Gly Ala Ser Gln Lys Ile Gln Leu Val Asn
                20                  25                  30

Thr Asn Gly Ser Trp His Ile Asn Arg Thr Ala Leu Asn Cys Asn Asp
            35                  40                  45

Ser Leu His Thr Gly Phe Leu Ala Ala Leu Phe Tyr Thr His Lys Phe
        50                  55                  60

Asn Ser Ser Gly Cys Pro Glu Arg Met Ala Ser Cys Arg Pro Ile Asp
```

-continued

```
            65                  70                  75                  80
Gly Phe Ala Gln Gly Trp Gly Pro Ile Thr Tyr Thr Glu Pro Asn Ser
                85                  90                  95

Pro Asp Gln Arg Pro Tyr Cys Trp His Tyr Ala Pro Arg Pro Cys Gly
                100                 105                 110

Ile Val Pro Ala Ser Gln Val Cys Gly Pro Val Tyr Cys Phe Thr Pro
                115                 120                 125

Ser Pro Val Val Val Gly Thr Thr Asp Arg Ser Gly Val Pro Thr Tyr
                130                 135                 140

Ser Trp Gly Glu Asn Glu Thr Asp Val Met Leu Leu Asn Asn Thr Arg
145                 150                 155                 160

Pro Pro Gln Gly Asn Trp Phe Gly Cys Thr Trp Met Asn Ser Thr Gly
                165                 170                 175

Phe Thr Lys Thr Cys Gly Gly Pro Pro Cys Asn Ile Gly Gly Val Gly
                180                 185                 190

Asn Arg Thr Leu Ile Cys Pro Thr Asp Cys Phe Arg Lys His Pro Glu
                195                 200                 205

Ala Thr Tyr Thr Lys Cys Gly Ser Gly Pro Trp Leu Thr Pro Arg Cys
                210                 215                 220

Leu Val Asp Tyr Pro Tyr Arg Leu Trp His Tyr Pro Cys Thr Leu Asn
225                 230                 235                 240

Phe Ser Ile Phe Lys Val Arg Met Tyr Val Gly Gly Val Glu His Arg
                245                 250                 255

Leu Asn Ala Ala Cys Asn Trp Thr Arg Gly Glu Arg Cys Asn Leu Glu
                260                 265                 270

Asp Arg Asp Arg Ser Glu Leu Ser Pro Leu Leu Leu Ser Thr Thr Glu
                275                 280                 285

Trp Gln Ile Leu Pro Cys Ala Phe Thr Thr Leu Pro Ala Leu Ser Thr
                290                 295                 300

Gly Leu Ile His Leu His Gln Asn Ile Val Asp Val Gln Tyr Leu Tyr
305                 310                 315                 320

Gly Val Gly Ser Ala Phe Val Ser Phe Ala Ile Lys Trp Glu Tyr Ile
                325                 330                 335

Leu Leu Leu Phe Leu Leu Leu Ala Asp Ala Arg Val Cys Ala Cys Leu
                340                 345                 350

Trp Met Met Leu Leu Ile Ala Gln
                355                 360
```